(12) United States Patent
Arkans

(10) Patent No.: US 11,000,444 B2
(45) Date of Patent: May 11, 2021

(54) TREATMENT DEVICES AND METHODS

(75) Inventor: Edward Arkans, Carlsbad, CA (US)

(73) Assignee: GNOTRIX, LLC, San Marcos, CA (US)

( * ) Notice: Subject to any disclaimer, the term of this patent is extended or adjusted under 35 U.S.C. 154(b) by 404 days.

(21) Appl. No.: 12/702,288

(22) Filed: Feb. 8, 2010

(65) Prior Publication Data
US 2011/0196269 A1    Aug. 11, 2011

(51) Int. Cl.
*A61H 9/00*    (2006.01)
*A61N 1/36*    (2006.01)
*A61H 1/02*    (2006.01)

(52) U.S. Cl.
CPC ......... *A61H 9/0078* (2013.01); *A61H 1/0262* (2013.01); *A61H 9/0092* (2013.01); *A61N 1/36003* (2013.01); *A61H 2201/0103* (2013.01); *A61H 2201/0157* (2013.01); *A61H 2201/10* (2013.01); *A61H 2201/1642* (2013.01); *A61H 2201/5002* (2013.01); *A61H 2201/5015* (2013.01); *A61H 2201/5061* (2013.01); *A61H 2201/5071* (2013.01); *A61H 2203/0406* (2013.01); *A61H 2205/106* (2013.01);
(Continued)

(58) Field of Classification Search
CPC .............. A61H 9/0078; A61H 2201/10; A61H 2205/108; A61H 2205/106; A61H 2205/10; A61H 2201/5002; A61H 2201/5015; A61H 2201/5071; A61H 2201/0103; A61H 2201/0157; A61H 2201/1238; A61H 2201/1253; A61H 2201/16; A61H 2201/164; A61H 2201/1642; A61H 2201/1645; A61H 2201/165; A61H 2201/1652; A61H 2201/1654; A61H 2230/305; A61H 2230/30; A61H 2230/04; A61H 2230/045; A61H 2203/004; A61H 2203/0406; A61H 2203/0425; A61H 2203/0431
USPC ............ 601/15, 84, 148–152; 606/201–204; 602/13; 128/DIG. 20, 898
See application file for complete search history.

(56) References Cited

U.S. PATENT DOCUMENTS 4,738,249 A * 4/1988 Linman .................. A61H 9/005
                                                                                         601/152
5,186,163 A * 2/1993 Dye ...................... A61H 9/0078
                                                                                         601/152

(Continued)

FOREIGN PATENT DOCUMENTS

WO    WO 2008056108 A1 * 5/2008 .......... A61H 9/0078
WO    WO-2008056108 A1 * 5/2008 .......... A61F 13/085

OTHER PUBLICATIONS

Ganesh Ramaswami, MD, PhD, et al., Rapid foot and calf compression increases walking distance in patients with intermittent claudication: Results of a randomized study, Journal of Vascular Surgery, May 2005, p. 794, vol. 41, No. 5 (Exhibit 1 attached to Sep. 28, 2015 Response to Office Action).

(Continued)

*Primary Examiner* — Jenna Zhang
(74) *Attorney, Agent, or Firm* — Henricks Slavin LLP

(57) ABSTRACT

Venous therapy methods and apparatus improve arterial or venous blood flow, for example in the legs. Venous therapy can reduce venous backflow and can improve arterial therapy such as that provided by intermittent pneumatic compression therapy.

50 Claims, 11 Drawing Sheets

(52) U.S. Cl.
CPC .... *A61H 2205/108* (2013.01); *A61H 2205/12* (2013.01); *A61H 2230/605* (2013.01)

(56) References Cited

U.S. PATENT DOCUMENTS

| | | | | |
|---|---|---|---|---|
| 5,711,760 | A * | 1/1998 | Ibrahim | A61H 9/0078 601/149 |
| 6,007,559 | A * | 12/1999 | Arkans | A61B 17/135 601/150 |
| 6,062,244 | A | 5/2000 | Arkans | |
| 6,358,219 | B1 | 3/2002 | Arkans | |
| 2005/0075531 | A1* | 4/2005 | Loeb | A61H 9/0078 600/17 |
| 2006/0074362 | A1* | 4/2006 | Rousso et al. | 601/152 |
| 2008/0255494 | A1* | 10/2008 | Rousso | A61K 31/44 602/62 |
| 2010/0137764 | A1* | 6/2010 | Eddy | A61H 1/008 601/152 |

OTHER PUBLICATIONS

Mail Clinic Staff; Diseases and Conditions—Claudication; http://www.mayoclinic.org/diseases-conditions/claudication/basics/definition/con-20033581; accessed and downloaded Sep. 28, 2015, pp. 1-7 (Exhibit 2 attached to Sep. 28, 2015 Response to Office Action).

Claudication; Wikipedia; pp. 1-3; HTTPS://EN.Wikipedia.org/wiki/claudication, pp. 1-3, accessed and downloaded Sep. 28, 2015 (Exhibit 3 attached to Sep. 28, 2015 Response to Office Action).

A. Berni, et al., Randomized study on the effects of different strategies of intermittent pneumatic compression for lower limb claudication; G Chir vol. 30, n. 6/7, pp. 269-273; Jun./Jul. 2009 (Exhibit 4 attached to Sep. 28, 2015 Response to Office Action).

Delis, K.T., et al., Optimum Intermittent Pneumatic Compression Stimulus for Lower-limb Venus Emptying; European Journal of Vascular and Endovascular Surgery, vol. 19, Mar. 2000, pp. 261-269.

* cited by examiner

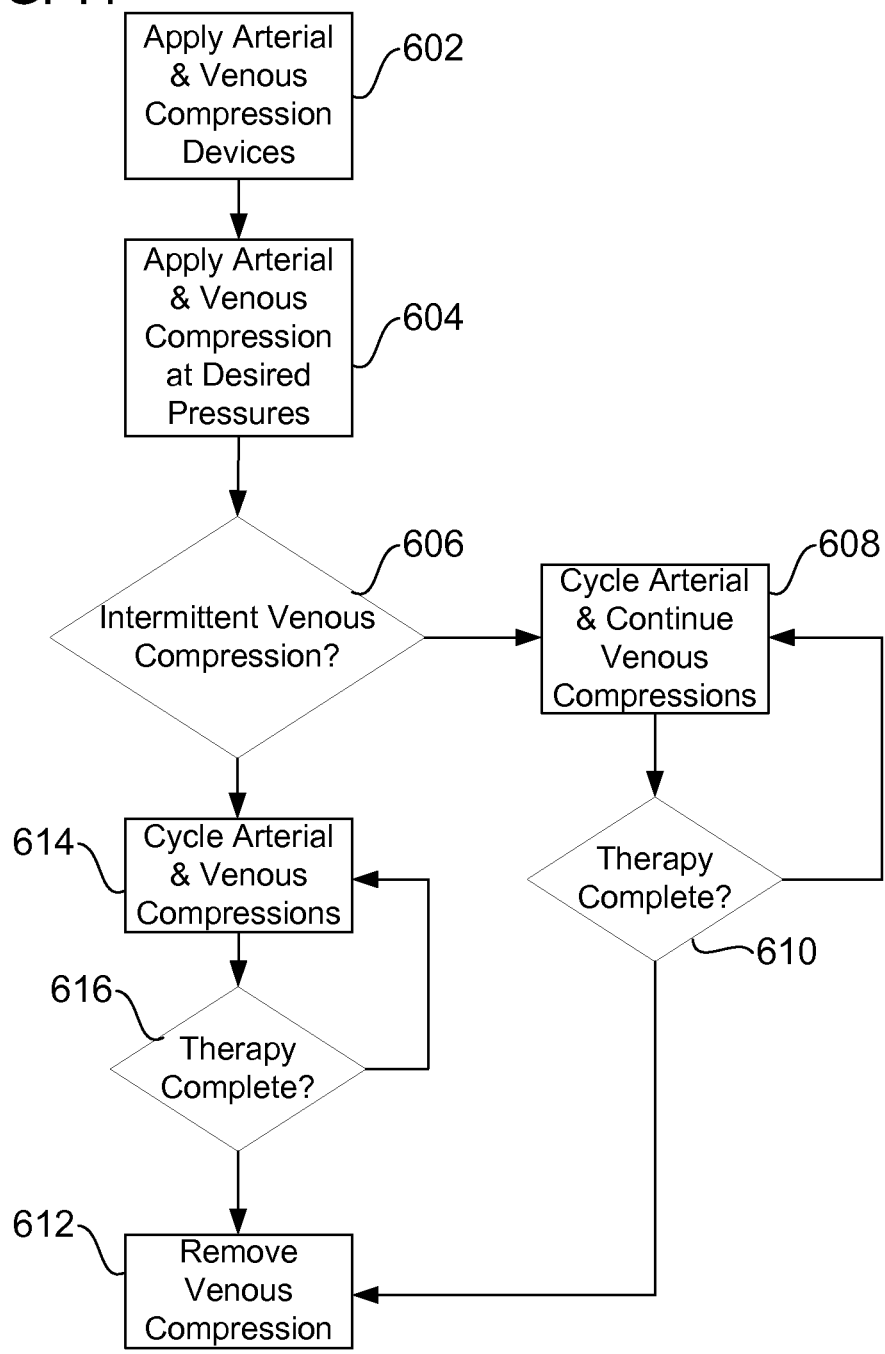

TREATMENT DEVICES AND METHODS

BACKGROUND

Field

This relates to arterial and/or venous therapy methods and apparatus, systems and procedures for improving arterial or venous blood flow, for example in the legs, and methods and apparatus for reducing venous backflow, for example in the legs and for example during therapy.

Related Art

Patients with obstructions of the arteries in the extremities or limbs, for example the leg (peripheral artery disease, or PAD) may experience reduced arterial blood flow, and possible additional complications as a result. Arterial blood flow may be improved by surgically bypassing the occluded arteries, or by removing obstructions with devices that are inserted into the blood vessel. The deterioration of arterial blood flow can lead to severe pain, tissue loss (arterial ulcers), or toe loss despite use of vascular procedures. When the arteries cannot be repaired anymore, the reduced arterial blood flow may require amputation.

Non-invasive techniques can be used to increase vascular blood flow without surgery. Devices may be used that apply a cycled compressive force to various designated areas of an extremity or limb, for example the foot or leg. This cycled compressive force is designed to increase the amount of blood returning to the heart through the veins, thereby enabling increased arterial blood flow to the limb.

More specifically, peripheral arterial disease of the lower limbs is treated medically and non-invasively using external intermittent pneumatic compression (IPC) devices that apply rapid, high-pressure pulses to the lower extremity, which may include areas of the foot, ankle, calf and thigh. Another well accepted medical treatment for the same disease is walking therapy where the patients are encouraged to walk; often using a treadmill. These two treatment modalities, IPC and walking have certain commonalities. Both are performed with the patients heart located above the affected lower limbs. Both involve rapid compression of the limb's veins: IPC by external compression and walking by muscle contraction. IPC typically applies a high pressure of short duration of several seconds followed by a much lower pressure of longer duration. Walking, consistent with the various phases of gait, applies a high pressure of short duration during muscle contraction followed by a relatively longer duration of lower pressure due to muscle relaxation. In both cases, vein compression is sufficient to completely collapse the vein and therefore empty the vein of its blood. The expelled venous blood within the foot, ankle, calf and thigh regions is typically moved toward the heart and one way check valves distributed along the lower extremity's veins prevent the reverse flow of that blood away from the heart and therefore, distally toward the foot.

When the patient is upright, either sitting or standing while at rest and without IPC, the veins are full and the pressure in those veins is the hydrostatic pressure equal to the height from that point of the vein to the heart multiplied by the density of the blood, multiplied by the acceleration of gravity (9.8 m/sec$^2$). Since the acceleration of gravity and blood density do not change, the venous pressure can be considered to be proportional to the height of the fluid in the vein below the heart. When the veins are emptied, either from walking, exercise or from IPC, the column of blood to the heart is interrupted and the venous pressure drops to close to zero. Herein, arterial compression from walking, exercise or IPC or from other forms of arterial compression also will be termed arterial therapeutic compression, or ATC. The time-averaged pressure in the arteries is the sum of mean arterial pressure created by the pumping heart and the hydrostatic pressure calculated similarly to venous pressure. Neither walking nor therapeutic IPC apply enough pressure to collapse the arteries so their pressure is not reduced as in the veins.

Flow through the capillaries from the arteries to the veins is therefore increased when the venous pressure is reduced and the arterial pressure is unchanged since flow is proportional to the pressure difference divided by the resistance to flow. This physiological mechanism is the most recognized cause of increased flow when using IPC in the treatment of PAD and also takes place during walking. This mechanism remains in place until the veins refill and reestablish higher venous pressures. In patients with properly functioning venous valves, the veins refill slowly from arterial inflow passing through the capillaries and into the veins. However, in patients with incompetent venous valves, blood falls rapidly backward through the limb's veins and rapidly creates the column of blood that rapidly reestablishes higher venous pressure. The physiological mechanism described above for increasing blood flow to the extremity is therefore lessened in its duration.

All of the veins in the legs have venous valves. The valves have two leaflets that allow blood to flow only in one direction. Venous blood normally moves along the veins toward the heart. The venous valves prevent the blood from falling back to a lower part of the leg, for example when the individual is standing, sitting or whenever the heart is above the limb. Normal valves thus prevent venous reflux, and therefore help to maintain the normal pressure difference between arterial blood and venous blood, and keeps venous blood from accumulating in the legs.

If the venous valves become damaged or do not function properly, blood can flow down the veins or away from the heart and accumulate in lower parts of the leg. The accumulated blood can produce vein enlargement, swelling in the leg with accompanying pain and other complications. Some surgical procedures can be used to improve venous blood flow, such as by removing superficial veins having the incompetent valves, but deep veins are not removed because of their importance to adequate flow of blood from the leg back to the heart. Other surgical procedures can also be used, but they require surgical access to the inside or the outside of the vein.

Accumulated blood due to incompetent venous valves reduces arterial blood flow from normal due to the presence of the venous blood, its associated column of pressure, and the reduced removal of the venous blood back to the heart. Therefore, the efficacy of any therapy for arterial disease or deficiencies in the legs is reduced in those patients with incompetent venous valves. Use of arterial pumps or other means for intermittent compression therapy in such patients may be ineffective or less effective. For example, it has been shown that patients with venous reflux in the leg obtain less physiological effect of increased arterial blood flow during IPC. Patients using IPC or walking to treat their PAD will therefore receive less effective treatment if they also have incompetent venous valves that allow venous reflux.

SUMMARY

Methods and apparatus can improve venous blood flow, including in patients having incompetent venous valves. Conventional therapeutic apparatus and methods can be improved, for example by reducing the effects of venous reflux and other effects of incompetent venous valves. Additionally, vascular therapies, for example and without limitation, ATC, can now be used on a class of patients for whom such therapies were not previously indicated or would not have been indicated based on conventional understanding. They can be used in conjunction with supervised or unsupervised exercise programs, including those for treatment of PAD. As used herein, vascular therapy encompasses arterial therapy, venous therapy and lymphatic therapy. These and other benefits may be provided by one or more of the apparatus or methods described herein.

In one example of a therapy system and procedure, vascular blood flow in a leg is improved over that in a non-treatment condition, for example a resting condition or a sitting position, by enhancing blood flow in the leg and collapsing one or more veins in the leg. In one example, arterial blood flow is increased using an external mechanism such as an arterial pump, for example those used in IPC therapy. In another example, arterial blood flow is increased in the leg at a location in the leg while generating sufficient pressure proximally of the location to collapse a vein in the leg. In a further example, arterial blood is pumped in the leg and pressure is generated in the leg cyclically. In an additional example, arterial blood is pumped in the leg and pressure generated in the leg intermittently. In another example, arterial blood is pumped in the leg and pressure generated in the leg greater than or equal to 20 mm of mercury or greater than or equal to approximately 20 mm of mercury. In a further example, pressure is generated in the leg at a location and pressure for arterial pumping and pressure is generated proximal to the location and less than the ATC pressure, and in another example approximately 10 mm of mercury less than the ATC pressure, which may be for example and without limitation an IPC pressure. In any of the examples described herein where pressure is applied or generated for arterial therapeutic compression, proximal pressure can be applied or generated (such as may be created through electrical stimulation to cause muscle contraction and therefore pressure applied to the vessels) that is more than 10 mm of mercury less than the arterial ATC pressure. In an additional example of arterial pressure being applied for arterial therapy where the arterial pressure is applied cyclically, proximal pressure is generated also cyclically. In another example where ATC is applied and proximal pressure is generated cyclically, the proximal pressure can be generated in a phase different from any arterial pressure cycle applied as part of ATC.

In another example, a therapy system and procedure generates a venous occlusion pressure during therapy. In one example, the venous occlusion pressure is generated over a span of time, and in another example generated repeatedly over a span of time. In another example, the venous occlusion pressure is generated during arterial therapeutic compression. In a further example, the venous occlusion pressure is generated under control of a control system, and one example being a manual control, and another example being electronic or electromechanical control. In an additional example, the venous occlusion can be part of other pressure apparatus applied to the patient. In yet another example, pressure is generated using electrical stimulation.

In another example of a therapy apparatus and procedure, an arterial pumping system is applied to the outside of a leg and an additional pressure is generated proximally thereof sufficient to collapse a vein. In one example, the additional pressure is greater than approximately 20 mm of mercury. In another example, the additional pressure is approximately 10 mm of mercury or more below the pressure applied by the ATC system, and in an additional example the additional pressure is simply less than the then-existing arterial pressure such that the blood can push past the venous occlusion. In a further example, the additional pressure is relatively constant, while in another example the additional pressure cycles. In an example where the arterial pumping system applies pressure cyclically, the additional pressure can cycle at a different phase. Alternatively, the additional pressure can cycle in an opposite phase. Where the arterial pressure and the additional pressure both cycle, the additional pressure can be high when the arterial pressure is low and decrease when the arterial pressure begins to increase. Additionally or alternatively, the additional pressure can rise when the arterial pressure decreases.

A further example of therapy apparatus and method may apply a pressure to or generate a pressure in a leg sufficient to collapse a vein in the leg where the patient suffers from incompetent venous valves. In one example, the pressure may be applied by a tourniquet, for example without limitation an inflatable pressure cuff, and in another example, the pressure may be applied through a phlebotomist tourniquet and in another generated through electrical stimulation. In a further example, the pressure may be applied through generation focused on a particular vein, such as the iliac vein or a saphenous vein, a deep or superficial vein, or through pressure to a region surrounding a vein.

In another example, a therapy apparatus and method may generate pressure in a leg sufficient to collapse a vein in the body and a therapeutic procedure applied to the body. In one example, venous occlusion is carried out using a tourniquet, and in some examples, the tourniquet may be a pressure cuff, or an elastic band or tape, and in another example, the venous occlusion is carried out using a venous occluder. As in any of the applications described herein using venous occlusion, venous occlusion can be carried out at a number of locations, including separately or simultaneously. In examples described in the present application, venous occlusion is carried out on a patient's leg, but can be carried out in other locations as well. Where the venous occlusion is in the patient's leg, the occlusion can be at any of a number of locations, including proximally or distally, and completely circumferentially of the leg or at discrete or multiple locations about a perimeter of the leg. The therapeutic procedure applied to the body may be a number of therapies, including but not limited to ATC, and therapies applied individually or in combination. In several examples described herein, the therapeutic procedure is applied over time, and may be applied over a matter of minutes or longer, and the therapeutic procedures may be applied repeatedly or having a frequency, which can be seconds, minutes or hours. In several examples described herein, venous occlusion is carried out while simultaneously taking steps to improve the patient's condition, for example but not by way of limitation through the therapeutic procedures described herein.

In a further example of a therapy system and method, an arterial pressure apparatus is placed on a patient's leg and a venous pressure configuration is applied proximal thereto and configured to produce venous collapse. The venous pressure configuration is configured to produce collapse of at least one venous vessel, and in another example it is configured to produce collapse of a plurality of venous vessels. In one example, the venous collapse pressure is approximately 20 mm of mercury, in another example greater than 20 mm of mercury, and in a further example between 50 and 70 mm of mercury. In a further example, the venous collapse pressure is 10 mm of mercury or more less than the applied arterial pressure. In another example, the arterial pressure apparatus cycles between at least two different pressures, and the venous pressure configuration also cycles between two different pressures. In one situation, the venous pressure configuration cycles between approximately 10 mm of mercury less than the applied arterial pressure and approximately no perceivable pressure. In another situation, the venous pressure configuration cycles low when the arterial pressure cycles high and vice versa.

In another example of a therapy system and method, a control system for an arterial pressure system and a proximal pressure system applies pressure to the arterial pressure system and pressure to the proximal pressure system. In one example, the proximal pressure system cycles between two different pressures. In another example, the proximal pressure system applies a pressure sufficient to collapse one or more veins or all of the veins. In a further example, the proximal pressure system has pressure applied to it sufficient to apply a perceived pressure to the patient's leg at least 20 mm of mercury, and in another example between approximately 50 and 70 mm of Hg. In an additional example, the arterial pressure system and the proximal pressure system cycle. In one situation, the proximal pressure system cycles low when the arterial pressure system is high and vice versa. In any of the examples described herein, firmware, software or other form of digital instructions can be used to implement the methods and procedures, and such may be stored and retrieved on any number of storage media types, including servers, ROM devices, hard drives, digital media devices and the like.

In an example of a process for improving vascular blood flow in a patient's leg, one or more and in several examples a large plurality of veins are collapsed, such as through generation of pressure while arterial pumping occurs for increasing arterial flow greater than resting or sitting conditions. In one example, pressure is produced sufficient to collapse a vein. In another example, arterial pumping occurs through pressure apparatus applied to the patient's leg and venous collapse pressure is generated proximal thereto. In a further example, arterial pumping occurs through pressure apparatus applied to the patient's leg at a first pressure and venous pressure is generated proximal thereto at a pressure approximately 10 mm of mercury less than the first pressure. In another example, arterial pumping occurs in cyclically and venous pressure is applied cyclically. In one situation, high venous pressure is generated when the arterial pumping pressure is low, and vice versa.

In another example of a process for improving vascular blood flow in a patient's leg, arterial pumping is applied externally to a patient's leg while reducing or restricting venous backflow or reflux. In one example, reflux is reduced by collapsing one or more veins. In another example, reflux is reduced by applying a pressure proximal to the arterial pumping greater than approximately 20 mm of mercury. In a further example, arterial pumping occurs with a high and a low pressure, and proximal pressure is applied when the arterial pumping pressure is low. In one situation, the proximal pressure is higher than the low arterial pumping pressure, and in another situation, the proximal pressure during at least one interval is higher than the arterial pumping pressure during the interval. In another situation, the proximal pressure is configured to rise as the arterial pressure drops, and in a further situation, the proximal pressure is configured to drop when the arterial pressure begins to rise.

It is noted that any of the apparatus and methods described herein can be used in therapy applications. For example, venous occlusion can be carried out over a span of time, and that span of time can be a matter of tens of seconds, minutes and even an hour, two hours, or more than two hours. For example, where arterial therapeutic compression is applied for a length of time, the venous occlusion can be carried out over the same length of time, whether the venous occlusion is static or intermittent or cyclical, and at least for a substantial period of time if less than the ATC time. Additionally, venous occlusion can be carried out repeatedly, whether intermittent or cyclical, over a span of time and that span of time can be a matter of tens of seconds, minutes and even an hour, two hours or more than two hours. In one example, where ATC is applied repeatedly, venous occlusion can be applied with the same frequency, and at least more than once during ATC. Often, venous occlusion is applied repeatedly within seconds or minutes of each other while ATC is applied.

These and other examples are set forth more fully below in conjunction with drawings, a brief description of which follows.

BRIEF DESCRIPTION OF THE DRAWINGS

FIG. 11 is a schematic of another process of patient therapy using a patient therapy system described herein.

DETAILED DESCRIPTION

This specification taken in conjunction with the drawings sets forth examples of apparatus and methods incorporating one or more aspects of the present inventions in such a manner that any person skilled in the art can make and use the inventions. The examples provide the best modes contemplated for carrying out the inventions, although it should be understood that various modifications can be accomplished within the parameters of the present inventions.

Examples of therapy systems and of methods of making and using the therapy systems are described. Depending on what feature or features are incorporated in a given structure or a given method, benefits can be achieved in the structure or the method. For example, therapy systems using inflatable or other controllable pressure applicator may achieve more consistent results, including for example when used with an IPC or related therapy system. They may also permit more flexibility in the application of the desired therapy regimen.

These and other benefits will become more apparent with consideration of the description of the examples herein. However, it should be understood that not all of the benefits or features discussed with respect to a particular example must be incorporated into a therapy regimen, therapy system or method in order to achieve one or more benefits contemplated by these examples. Additionally, it should be understood that features of the examples can be incorporated into a therapy system or method to achieve some measure of a given benefit even though the benefit may not be optimal compared to other possible configurations. For example, one or more benefits may not be optimized for a given configuration in order to achieve cost reductions, efficiencies or for other reasons known to the person settling on a particular product configuration or method.

Examples of several therapy system configurations and of methods of making and using the therapy systems are described herein, and some have particular benefits in being used together. However, even though these apparatus and methods are considered together at this point, there is no requirement that they be combined, used together, or that one component or method be used with any other component or method, or combination. Additionally, it will be understood that a given component or method could be combined with other structures or methods not expressly discussed herein while still achieving desirable results.

It should be understood that terminology used for orientation, such as front, rear, side, left and right, upper and lower, and the like, are used herein merely for ease of understanding and reference, and are not used as exclusive terms for the structures being described and illustrated.

Figure 1:
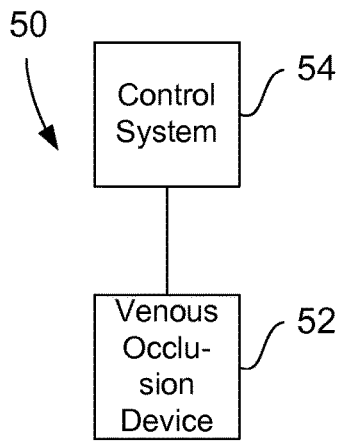
FIG. 1 is a schematic of an example of a venous occlusion system for use in one or more of the examples described herein.

A venous occlusion system 50 (FIG. 1) can be used in a number of therapeutic applications, including therapeutic reduction of venous reflux, in combination with arterial therapeutic compression, and the like. The venous occlusion device 52 is applied to the patient at an extremity or a limb, for example a leg. The venous occlusion device 52 can be a pressure cuff, an elastic band, a localized pressure applicator, a suitably configured electrical stimulation device or another device that produces venous occlusion. For present purposes, "venous occlusion" means substantially collapsing a vein. "Substantially collapsing a vein" is at least 50% reduction in cross-sectional area or in blood flow in the vein compared to that when no pressure is applied. The venous occlusion device 52 is controlled by a control such as control system 54. The control system 54 establishes venous occlusion as applied by the device 52. The control system may be a controller, an inflation pump such as a powered pump or an inflation mechanism such as an inflation bulb, or the control system may be as simple as a switch, knot or fastener used to set the occlusion device.

The venous occlusion system 50 can be used for therapy and applied over a span of time, or it can be applied in conjunction with other apparatus or procedures. For example, it can be applied in conjunction with arterial compression therapy, including IPC or other modes of arterial therapeutic compression. It can be carried out repeatedly, for example to produce a desired result.

Figure 2:
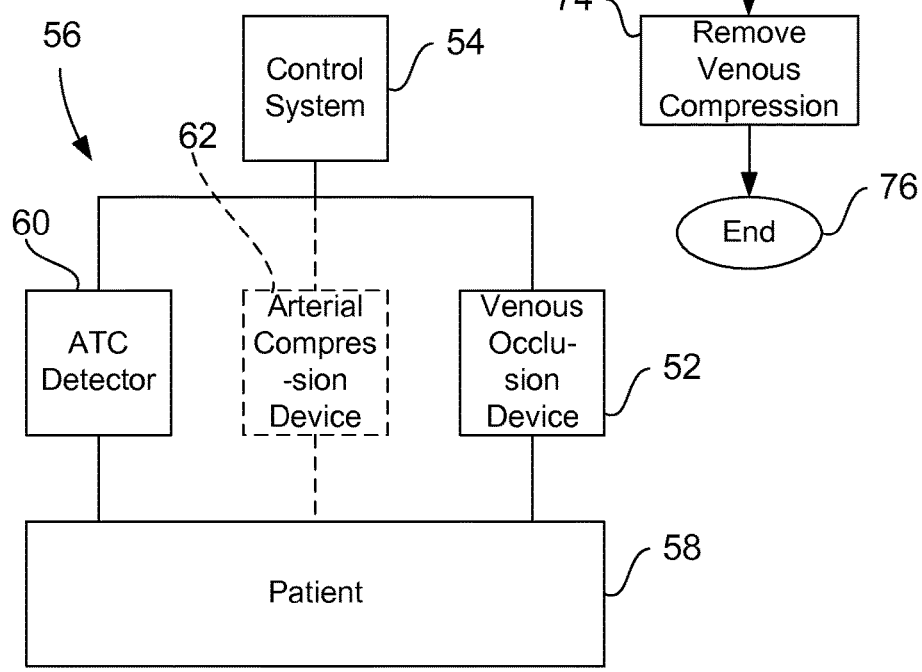
FIG. 2 is a schematic of another example of a venous occlusion system for use in one or more of the examples described herein.

In another example of a venous occlusion system, a venous occlusion system 56 (FIG. 2) includes the control system 54 and the occlusion device 52, that may be applied to a patient shown schematically for ease of illustration at 58. The occlusion system in the present example also includes an arterial therapeutic compression detector 60 the detector 60 can be a sensing device for sensing ATC, for example a muscle contraction sensor, a compression sensor, a limb flexion or extension sensor or other device such as those described herein for indicating that arterial therapeutic compression is occurring. The detector 60 can be as simple as visual confirmation of ATC. The venous occlusion system 56 may, if desired though it need not, include an external arterial compression device 62 operated by the control system 54 and applied to the patient 58. With external arterial compression, the venous occlusion device 52 can operate in conjunction with the arterial compression device to improve therapy. The arterial compression device 62 can be controlled by the control system 54, and suitable apparatus and methods can be used to allow coordinated operation of the venous occlusion device and the arterial compression device.

Figure 3:
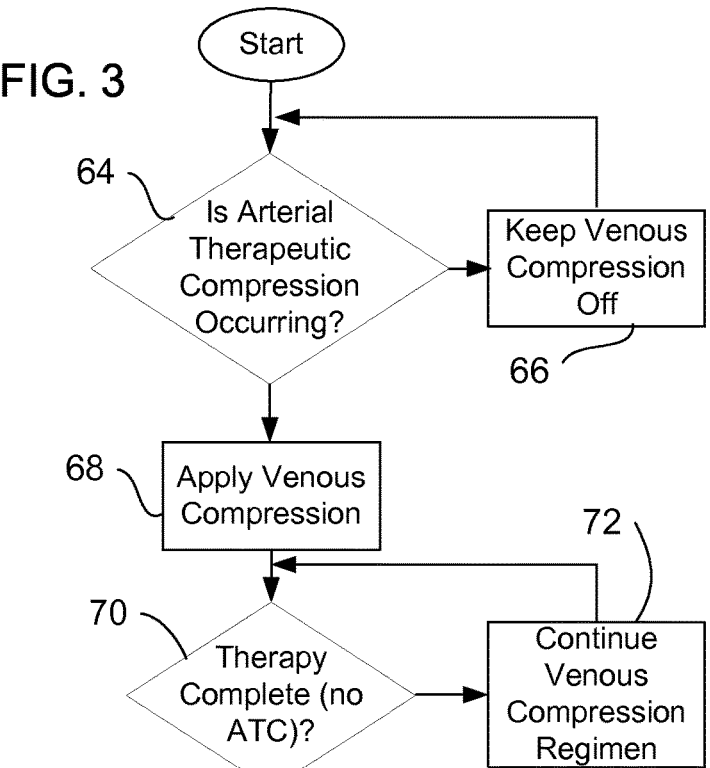
FIG. 3 is a general flowchart representing processes that can be used for venous occlusion with one or more of the examples described herein.

The processes with which either or both of the occlusion systems 50 and 56 will operate depend on the sophistication of the system. A simple mechanical system can be operated manually, but will be more difficult to achieve coordinated venous occlusion and arterial compression, for example. However, in one example, as depicted in FIG. 3, the system is checked 64 to see if arterial therapeutic compression is occurring. If not, the venous occlusion device is kept 66 in an off configuration so that venous blood flow is not inhibited. If there is arterial therapeutic compression, venous compression can be applied 68 using a suitable venous occlusion device. The venous compression can continue as desired, and may continue as long as arterial therapeutic compression is applied. A regular check is made 70 to see if the therapy is complete, for example no arterial therapeutic compression. If ATC continues, the venous compression regimen is continued 72. If ATC is stopped 74, then venous compression is removed, and venous occlusion therapy is ended 76. In the present process, venous occlusion can be carried out using any of the apparatus and systems described herein or understood by one skilled in the art based on the description herein, and ATC can be according to any of the modalities described herein or understood by one skilled in the art based on the description herein.

Figure 4:
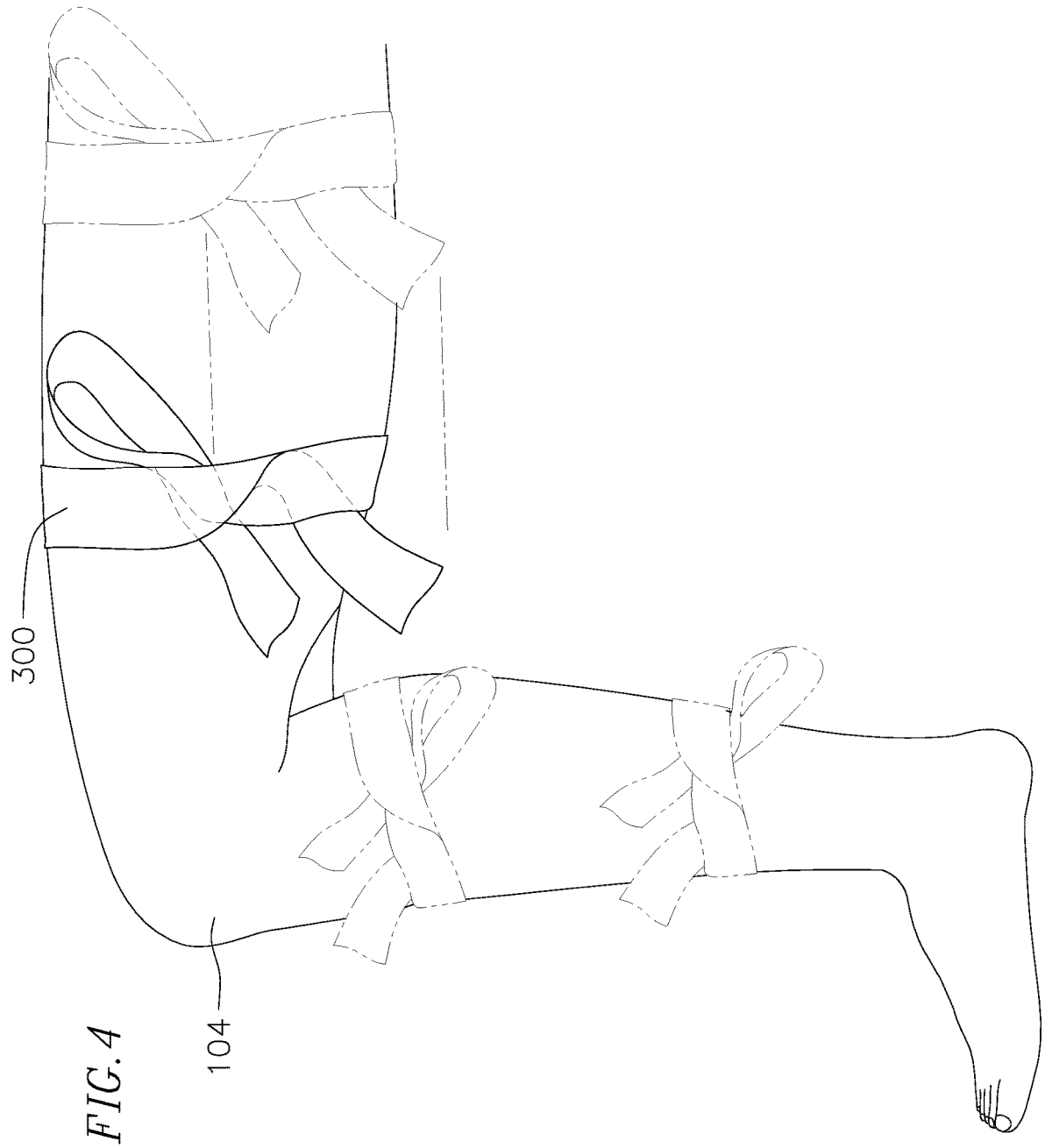
FIG. 4 is a side elevation view and partial schematic of a patient therapy system configured for use on a patient's leg.

In another example, a vascular therapy system 100 (FIG. 4) can be used to improve vascular blood flow in a patient's leg beyond that which might exist in a patient's leg when the patient is at rest or in a sitting position. In the example shown in FIG. 4, an external arterial compression apparatus 102 is applied to the foot and calf of the patient's leg 104, which is shown in FIG. 4 with the patient in a sitting position. The external arterial compression apparatus 102 may also have a thigh portion or extend to the thigh (not shown). The compression apparatus is coupled to a compression system such as that described more fully below for producing the desired compression having the desired compression profile. In other examples (not shown), the arterial compression apparatus can take other configurations, including without limitation foot only compression, calf only compression, thigh only compression, multiple compression pads for the foot, multiple compression pads for the calf, for the thigh, as well as combinations of the foregoing. Additionally, and without limitation, arterial compression can be done other than externally, such as by walking or other movement modalities or other forms of ATC. However, the examples of arterial compression described herein will be in the context of externally applied apparatus and walking for purposes of ease of illustration and discussion.

Figure 5:
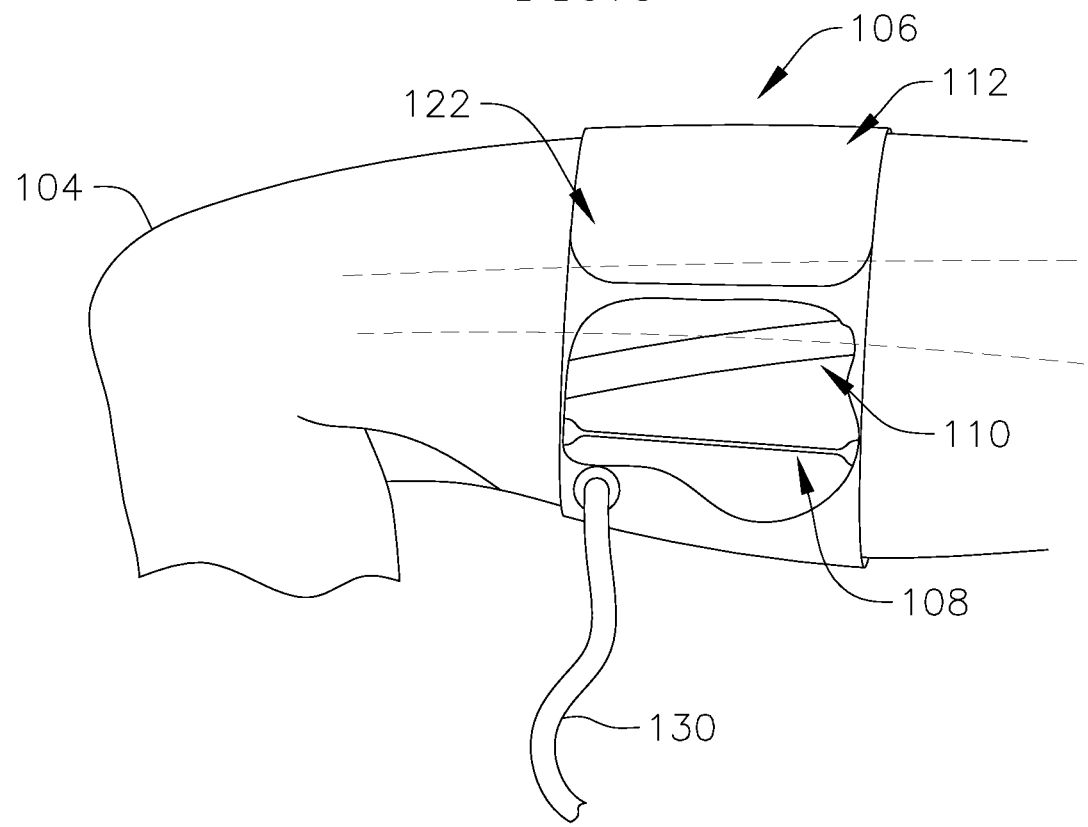
FIG. 5 is a side elevation view of a venous compression system for use with the assembly of FIG. 4.

The vascular therapy system 100 in the example of FIG. 4 also includes a venous pressure device 106. In the present example, the venous pressure device 106 is configured to be able to collapse a vein in the patient's leg, for example proximal of the compression apparatus 102. For example, the venous pressure device 106 can collapse superficial veins in the leg, in a further configuration the venous pressure device can collapse superficial and intermediate veins of the leg, and in another configuration the venous pressure device 106 can collapse deep veins in the leg in addition to superficial and intermediate veins. The venous pressure device can also be used during therapy for purposes additional to venous compression. In one example described herein, the venous pressure device can be used for arterial compression and before or after for venous compression. For example, during one part of a cycle, the venous pressure device applies arterial compression, such as that described in U.S. Pat. No. 6,007,559 for the thigh cuff, and during another part of the cycle the venous pressure device applies venous compression, such as that described herein. Depending on the configuration, the venous compression device can be applying a compression pressure at all times during therapy or cyclically or intermittently. In any case, the configuration of the venous pressure device 106 as positioned on the patient for use will depend on the desired application or applications. For purposes of collapsing a vein, the venous pressure device 106 applies pressure to the leg, in the example shown in FIGS. 4-6 the pressure being applied to the patient's thigh, a collapsed vein 108 is depicted schematically in FIG. 5 as a result of pressure applied by the venous pressure device 106. The collapsed vein 108 and an unaffected artery 110 are shown in FIG. 5 schematically through a cutaway view of the venous pressure device 106 and through the various tissue layers of the thigh. In the present examples, the venous pressure device 106 applies pressure to one or more veins while leaving the artery substantially unaffected.

As used herein, "compression pressure" is that pressure that produces the desired compression result. Compression pressure will be sufficient to produce tissue compression in the patient, and for blood flow compression that produces a hemodynamically significant result. Arterial compression pressures are pressures applied during arterial therapeutic compression, well known to those skilled in the art. Venous compression pressures are those producing the desired venous compression, and for venous occlusion, the venous compression pressures are those that produce venous occlusion.

Figure 6:
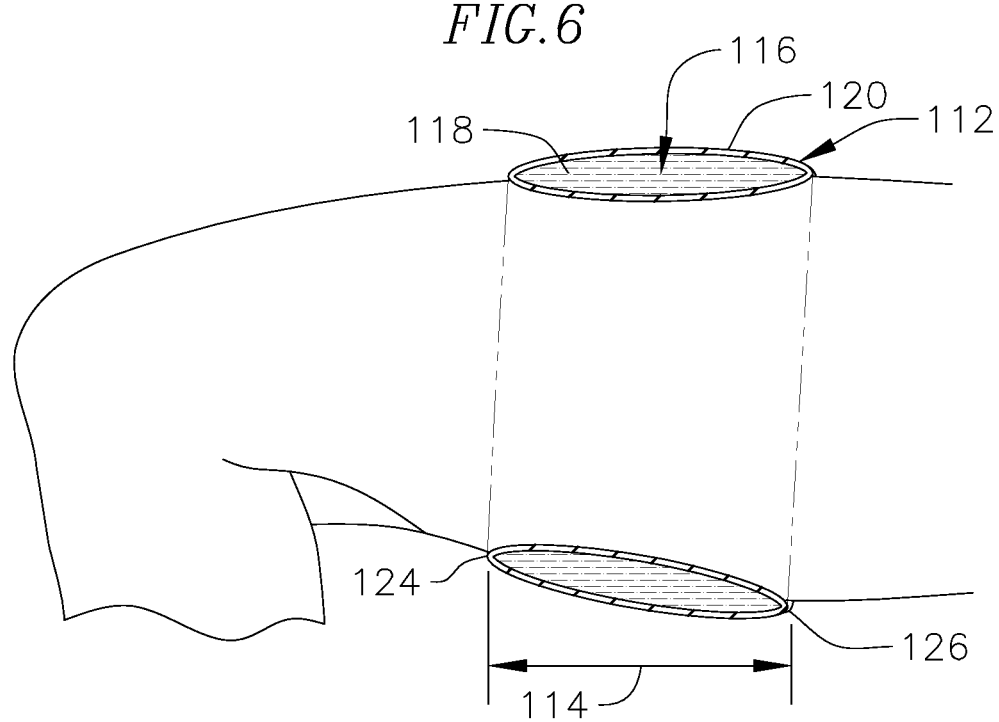
FIG. 6 is a side elevation and partial longitudinal section of the venous compression system of FIG. 5.

In the example of the venous pressure device 106 in FIGS. 4-6, the venous pressure device 106 is substantially similar to conventional fluid-based blood pressure cuffs to the extent that it includes a cuff assembly 112 extending completely around the thigh. In the present example, the cuff assembly 112 extends completely around the patient's thigh for reliable positioning of the cuff assembly and application of pressure as desired. As shown in FIG. 6, the cuff assembly 112 includes a longitudinal length 114 and extending distally and proximally from a center of the cuff assembly, and a radial depth depending on the extent of filling or inflation of the cuff assembly. In the present example illustrated in FIGS. 4-6, the cuff assembly includes a fluid bladder 116, which may be suitable for receiving a fluid 118 such as air, oxygen, nitrogen, a liquid or other fluid as desired. The fluid bladder 116 may be enclosed within and protected by a suitable covering 120, as would be conventional. The cuff assembly also includes a retaining structure 122 (FIG. 5) for securing the cuff assembly at the desired location on the patient's limb. The retaining structure 122 may use a pile material such as that used in conventional hook and loop fastener combinations commonly known as Velcro®. Other securing configurations can be used.

In the configuration of the cuff assembly 112 shown in FIGS. 4-6, the length 114 of the cuff assembly is defined in part by the configuration of the bladder 116 and its protective covering 120. The particular form and application of pressure to the patient's limb can be configured as desired, but in the present example, the distal and proximal edges 124 and 126, respectively, produce edge pressure effects resulting in a lower application of pressure at the edges relative to that at the center of the cuff assembly. Additionally, the length 114 can be selected so as to apply the desired pressure profile spatially from the distal edge 124 to the proximal edge 126. The length in one example may be about 10 cm. In the present example, the application of pressure to the patient's thigh is substantially uniform interior to the distal and proximal edges. Also in the present example, the cuff assembly 112 applies a relatively consistent pressure to the patient's thigh around the perimeter of the thigh.

In other configurations (not shown), the venous pressure device can apply pressure to one or more veins in the patient's limb other than uniform pressure around the perimeter of the limb. For example, by selecting the locations and the configuration of the pressure devices, a pressure device may be held against a desired portion of a limb for applying localized pressure or applying the desired form of pressure. For example, the venous pressure device can apply pressure through focused application of pressure to an area rather than a perimeter, shaped application of pressure other than a uniform length such as the pressure cuff shown in the example of FIGS. 4-6, or in other configurations. The pressure application can be partially circumferential of the limb. A desired pressure application profile can be selected in part as a function of the configuration of the venous pressure device, and the venous pressure device can be in the form of a cuff, a patch or applicator applied to the patient's limb, or other application structure.

The inflatable or fillable bladder 116 is one example of compression means for applying or generating a compressive force to selected portions of the patient's limb. Other structures for applying compression may include but are not limited to tourniquets, including but not limited to pressure cuffs and elastic bands, blunt projections, focused applicators, distributed but discreet pressure application devices, an electrical stimulation electrode or electrodes, and the like. Other structures for applying compression may include but are not limited to bladder configurations of a single bladder, multiple bladder, differently-shaped bladders, bladders with flow restrictions or baffles, or the like.

While a single limb is depicted in the Figures, it is understood that the present discussion can be directed to more than one limb. For example, separate therapy devices can be applied to both of a patient's limbs, or a single therapy device can be configured to apply therapy to both of a patient's limbs, for example either simultaneously or alternately.

In the example of the venous compression device 106 shown in FIGS. 4-6, pressure in the device is increased or decreased through a conventional fluid conduit 130 (FIGS.

1-2) such as plastic tubing. In the present example, the venous compression device 106 includes a filling or an inflation source 132, which in the present example includes an inflation bulb 134 and a control valve or release valve 136, such as are included in conventional pressure cuffs. A pressure indicator or pressure gauge 138 is positioned in the inflation source 132 distal of the control valve 136. The pressure indicator provides a readout of the pressure applied to the leg 104 through the pressure cuff 112. The venous compression device 106 may also include a pressure relief valve 140 coupled to the fluid conduit. The pressure relief valve 140 helps to maintain a desired pressure in the venous compression device 106 the valve 140 can take a number of configurations, and in the present example takes the form of a spring-loaded or biased check valve. Alternatively, though not by way of limitation, the valve 140 may be mechanical, electrical or electromechanical, and may include for example and not by limitation a weight-loaded check valve, a spring, mechanical switches, electrical switches, electrical pressure transducers, a threshold-activated pressure switch or other pressure-dependent device. Other forms of filling or inflation sources may also be used or incorporated in the venous compression device 106.

One example of an external arterial compression apparatus 102 (FIG. 4) includes a compression sleeve 142 one having one or more inflatable chambers, for example at 144. Examples of compression devices are shown and described in U.S. Pat. Nos. 6,007,559, and 6,358,219, both of which are incorporated herein by reference. In the example shown in FIG. 4, the compression sleeve 142 has a single inflatable chamber, but multiple chambers can be provided, spaced apart, side-by-side or in other configurations. Therefore, the inflatable chamber can have one continuous chamber or may be subdivided into a plurality of individual, smaller inflation sub-chambers to provide the desired compression. In the present example, the compression sleeve 142 is shown as being disposed around the patient's calf, above the ankle and below the knee, but one or more compression sleeves of an external arterial compression apparatus can be placed at various locations on the limb. Additionally, the compression sleeve 142 can be sized and shaped to conform to the calf shape of a significant cross-section of the population, or the compression sleeve can be shaped to be more generic.

The compression sleeve 142 includes positioning straps 146 extending around the patient's leg. The positioning straps 146 help to hold the calf compression sleeve 142 in place. The straps 146 may also be configured so as to conform to the shape of the calf at the longitudinal position at which the compression sleeve is intended to be placed. The straps form means for retaining the inflatable chamber of the sleeve 142 substantially against selected portions of the limb. The straps may be secured to other parts of the compression sleeve through hook and loop material such as Velcro and/or buttons, snaps, adhesives or other fastening devices for securing the compression sleeve in place.

The compression apparatus 102 also includes in the present example a foot compression portion 148. The foot compression portion 148 is located on and applied to portions of the foot distal to the calf compression portion. The foot compression portion includes one or more inflatable chambers, such as those described in the two patents referenced above. The foot compression portion may include a single inflatable chamber or may have multiple chambers arranged as desired. The foot compression portion 148 can be sized and shaped to conform to the foot shape of a significant cross-section of the population, or can be shaped to be more generic. Additionally, the foot compression portion may include one or more positioning straps 150, including an ankle portion for retaining around the ankle, an arch portion for the upper tarsal region of the foot and a forward portion for the tarsal region of the foot. Other configurations can also be used. The straps form retaining means and may include secure meant devices such as a hook and loop material, buttons, snaps, adhesives or other fastening devices for securing the foot compression portion in place. Additionally, the foot compression portion can be secured to the calf compression portion, such as through an ankle strap 152. The ankle strap can be configured as shown in the Figures and may include retaining means in a manner similar to that of the other straps. Likewise, though not shown, the arterial compression apparatus 102 and the venous compression device can be secured to each other, such as through a knee strap behind, beside or in front of the knee. The ankle strap can be configured to include retaining means in a manner similar to that of the other straps. Other configurations may have the arterial compression apparatus and the venous compression device more completely integrated with one another with more than simply a strap.

Each bladder or other pressure generating component in the exterior arterial compression system in the present example of FIG. 4 is operated or controlled through a respective connective member, 154 and 156. Where the pressure generating components are fluid-filled bladders, pads or other expandable components, the connective member is a fluid conduit for communicating fluid from a fluid supply to the respective expandable component. Where the pressure generating component takes another form, such as a mechanical or electromechanical configuration, the connective member may be a conductor such as a wire or other suitable control element. In the present example of FIG. 4 where the connective member is coupled to a fluid bladder, the connective member is a fluid tube, and is coupled to the respective bladder through a removable connector 158 and 160 through respective fittings 162 and 164. Other means may be provided for gaining access to the pressure generating/application devices than fluid conduits and connectors and fittings.

Figure 8:
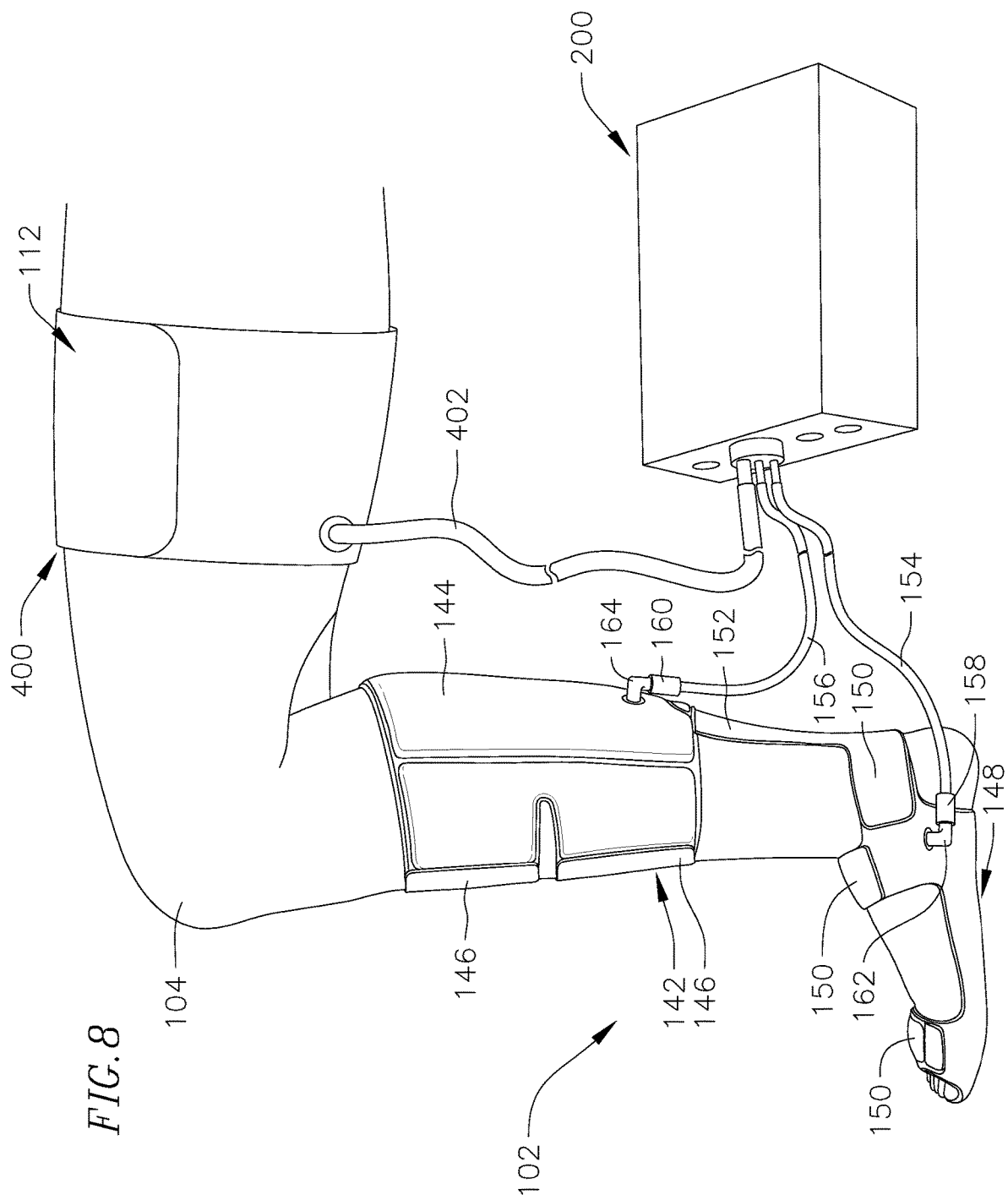
FIG. 8 is a side elevation view of another patient therapy system configured for use on a patient's leg.

The exterior arterial pumping system can be controlled manually in a manner similar to that described with respect to the venous compression system 106. The pressures and timing applied to the exterior arterial pumping system would be those conventional and existing systems. However, in examples described herein incorporating an exterior arterial pumping system, the compression achieved by application of pressure according to a given timing sequence can also be carried out using a configurable or controllable treatment device such as an IPC treatment device. One example of such a treatment device is controller 200 (FIG. 8-like components in the drawings have identical reference numbers), incorporating conventional electronics, including without limitation a processor, programmable components, one or more memory components, input and output components, one or more data entry components, electromechanical components, pneumatic components, display components and a power supply coupled to an electrical source through a power cord (not shown) or through a portable energy source such as a battery. In the present example, the controller 200 includes an accumulator having means for maintaining pressure during use of the apparatus, but the accumulator can be omitted or not used if the pressure developed by the pump is sufficient to achieve the desired pressure and time characteristics. Pressure can be maintained using an air tank, or other storage elements such as a spring-loaded diaphragm, spring-loaded piston cylinder, or other apparatus. The controller 200 controls and maintains the pressure in the exterior arterial pumping system according to the configurations and processes known to those skilled in the art.

In one conventional system, the accumulator includes an accumulator valve to help maintain a desired pressure level, which valve may be a spring-loaded check valve, pressure switch or other configurable control device. The accumulator also includes a pump, which may be internal or external, and which may include a piston and cylinder or a diaphragm arrangement for fluid compression and a motor for operating the piston or diaphragm arrangement. The system also includes a pressure regulator, which may maintain a pressure level of between 20 mm of mercury to about 150 mm mercury, or other selective pressure levels. The pressure regulator may include a pressure switch, transducer or other device to monitor the pressure and communicate with regulator valves to allow fluid to flow to the foot and calf or other limb area compression portions. The pressure regulator may be configured to independently control the pressure in each pressure-producing component, such as the inflatable bladders in the foot, ankle, calf and/or thigh compression portions. A pressure regulator can take the form of a fluid-activated solenoid valve, rotating aperture discs, and electrical coil with linear or rotational translation, or other structures for controlling pressure in the pressure-applying components. Additionally, the pressure regulator can be coupled to one or more regulator valves between the controller 200 and the respective fittings 162 and 164.

In application, with reference to the apparatus in FIGS. 4-6, the venous compression system 106 is placed 202 (FIG. 9) on the patient's leg 104. When used in combination with IPC therapy in the form of an external arterial pump system, the IPC therapy is begun and at the same time as, immediately before or immediately after, the venous compression cuff assembly 112 is inflated 204 to a pressure sufficient to collapse the underlying veins but not the underlying arteries. Intermittent compression pressures in IPC systems are typically above 60 mmHg and usually about 90-140 mmHg. In one example, the applied pressure can be in the range of 50 to 70 mm of mercury, and in the context of the IPC system, the applied pressure can be approximately 10 mm of mercury less than that applied by the IPC system. Also in the context of the IPC system, the applied venous compression pressure can be more than 10 mm of mercury below that applied by the IPC system, and in such an example can be still higher than the normal venous pressure at the level of the venous compression cuff. In another example, the applied venous pressure is between approximately 50 and 60 mm of mercury, and in a further example it is approximately 50 mm of mercury. In other examples, for example where the IPC applied pressure is approximately 120 mm of mercury, the applied venous pressure is less than 120 mm of mercury, and may be for example 110 mm of mercury. When one or more of these pressures are not applied, for example where a particular patient may not fit a typical profile for vascular therapy, the applied venous pressure using the venous pressure cuff 112 is selected so that the IPC therapy system as applied to the patient is sufficient to push the venous blood past the venous pressure cuff 112. In other situations where one or more of the foregoing pressures are not applied, such as in an example where a particular patient may not fit a typical profile for vascular therapy, the applied venous pressure can be selected so as to be at least 20 mm of mercury, and if capable of calculation or estimation, sufficiently high to collapse a significant number of veins in the area of application of the venous pressure. Another measure of venous pressure application, if capable of evaluation, is to apply a venous pressure sufficient to reduce venous reflux. One measure of reducing venous reflux is at least a 10% reduction, but a reasonable target is in the range of at least 40 to 60% reduction in venous reflux. Another measure for producing venous occlusion may be that pressure sufficient to reduce the vein cross sectional area while still allowing blood flow through the vein under muscle action, such as by walking.

In another application of a venous compression system, for example with or without an external arterial pump systems such as that shown in FIGS. 4-6, a venous compression system is applied to the patient's limb. An applied pressure is developed in the venous compression system that will be sufficient to collapse veins in the limb. In one example, the applied pressure is sufficient to collapse a substantial number of veins in the limb without collapsing the arteries. In one example, the pressure applied through the venous compression system is applied when the IPC therapy system is being used, for example when the patient is seated. In another example, the pressure is applied through the venous compression system without an IPC therapy system but where blood is pumped through the veins, for example while the patient is walking. During walking therapy, the venous compression system has pressure applied to it either at the same time as, immediately before or immediately after initiation of the walking therapy. The actual applied pressure may be capable of calculation or approximation, for example as a function of the distance below the heart that the venous compression cuff 112 is placed (the height differential between the venous compression 112 and the patient's heart, multiplied by the blood density and by the gravitational constant). In any of the examples described herein, the actual applied pressures through the venous compression system described above in conjunction with the apparatus in FIGS. 4-6 are believed to be suitable. In other examples, the ATC can be cycling, stair navigation, elliptical exercise equipment and other lower limb exercises. The application of the venous compression system can be used in conjunction with supervised or unsupervised exercise programs, including those for treatment of PAD, for example without limitation intermittent claudication.

In any of the examples described herein, a venous compression system, including without limitation that described with respect to FIGS. 4-6, is applied in an area of the limb where venous reflux can be reduced. In one example, the venous compression system is positioned where a substantial number of veins can be collapsed through the venous compression. In the example shown in FIG. 1, the venous compression system 106 is applied proximally of the IPC compression system 102. In the context of the patient's leg shown in FIG. 4, the venous compression system can be applied anywhere proximal of the compression sleeve 142, for example anywhere from below the knee to the groin area. While the position of the venous compression system of FIG. 4 is shown at an acceptable location on the patient's leg, other positions on the leg are also acceptable, such as proximal of the proximal-most IPC compression sleeve, and one reason for illustrating the venous compression system as shown in FIG. 4 is for clarity of the illustration.

Figure 13:
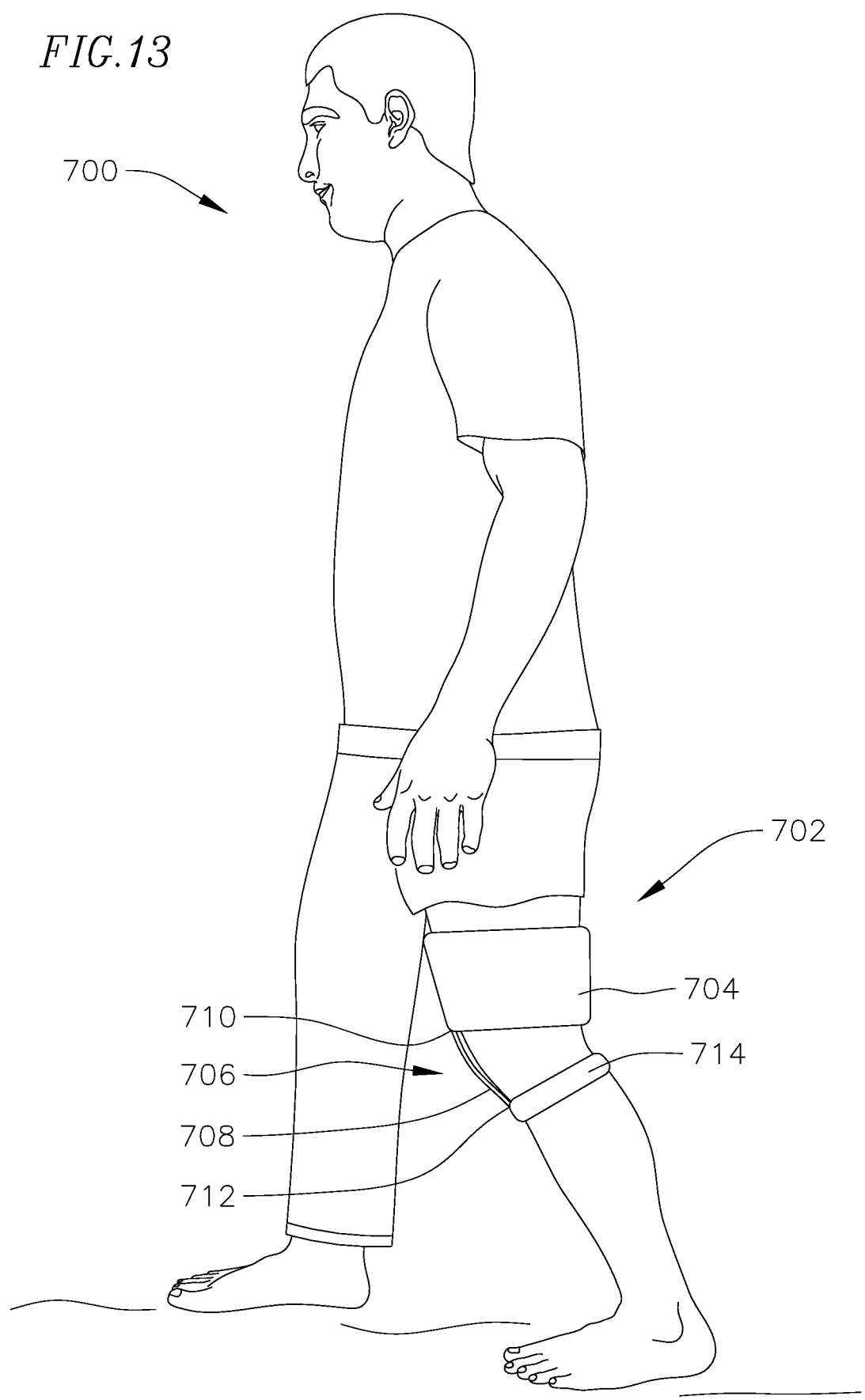
FIG. 13 is a representation of a venous occlusion system according to one of the examples described herein used in conjunction with arterial therapeutic compression.
Figure 14:
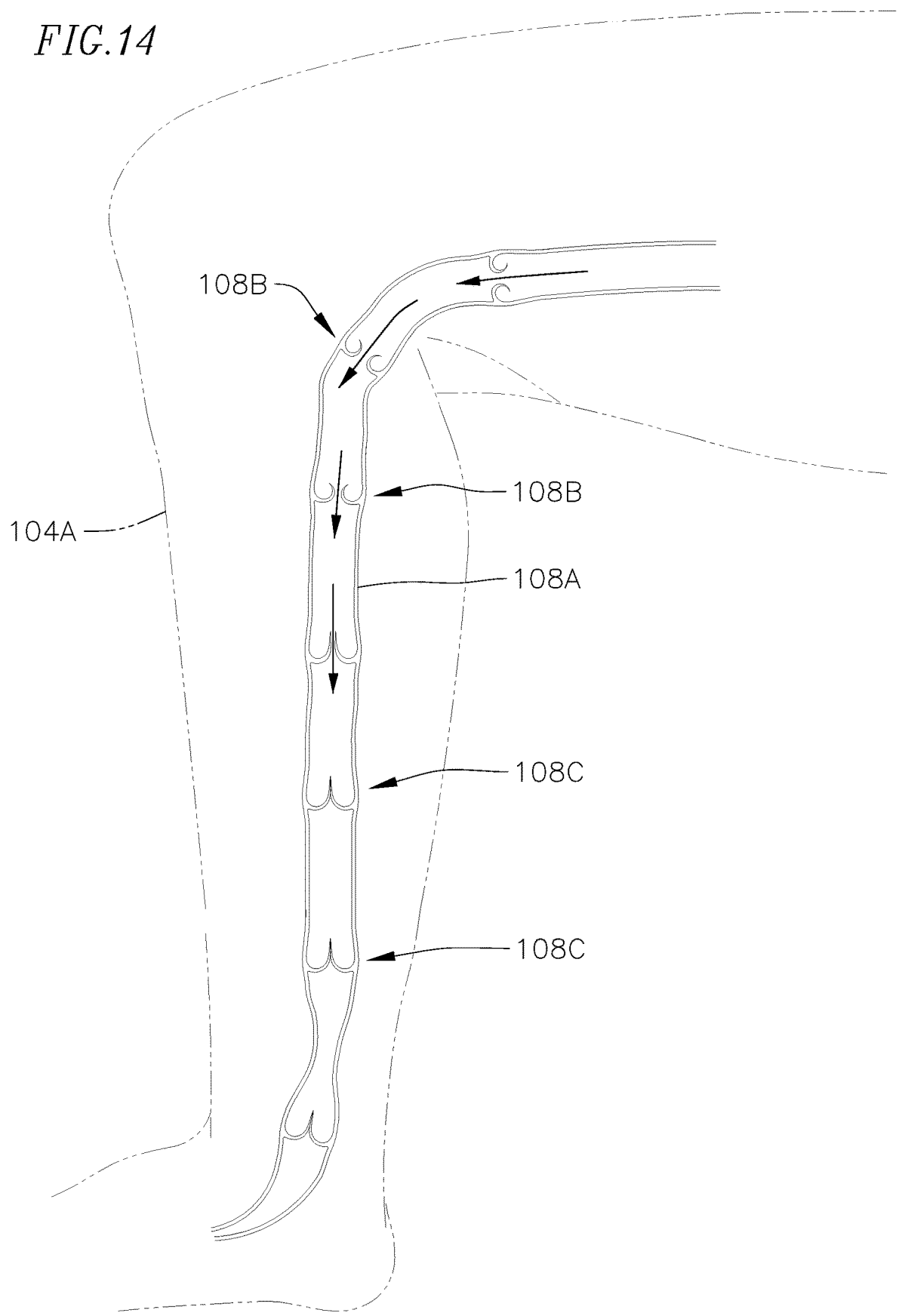
FIG. 14 is a schematic representation of a longitudinal cross-section of a leg vein showing venous valves.

As shown schematically in FIG. 13, a patient's leg 104A includes a vein 108A with a number of venous valves. The valves 108B are illustrated as not closing properly and would be considered incompetent venous valves. The valves 108C would be considered normal venous valves. In considering possible locations of any of the venous compression systems described herein, one consideration may be the location of incompetent venous valves versus the location of normal venous valves. If the location of an incompetent venous valve is known, the venous compression system 106 can be placed in an area of the incompetent valve or proximal or adjacent there to. Additionally, in the context of the theoretical distribution of the valves shown in FIG. 13, and IPC system such as that described with respect to FIG. 4 can be applied to the patient's leg and a suitable venous compression system applied to the patient's leg just below the knee in the area of one of the incompetent venous valves 108B. Alternatively, a venous compression system can be applied proximal there to, or a venous compression system can be applied distal thereto, and in one example still proximal to a proximal-most IPC cuff. Other means of selecting the location of a venous compression system can be used.

In any of the venous compression systems described herein, a therapist or a programmed control system (described more fully below) can determine 206 (FIG. 9) whether or not the venous compression applied to the limb is to be intermittent or cyclical or static. If the applied venous compression is to be static, the venous compression is continued 208 until the therapy is complete (such as walking therapy, external IPC therapy, or otherwise), or until the venous compression is to be discontinued. If the venous compression therapy is complete 210, venous compression is removed 212, and the venous compression cuff is removed.

Figure 9:
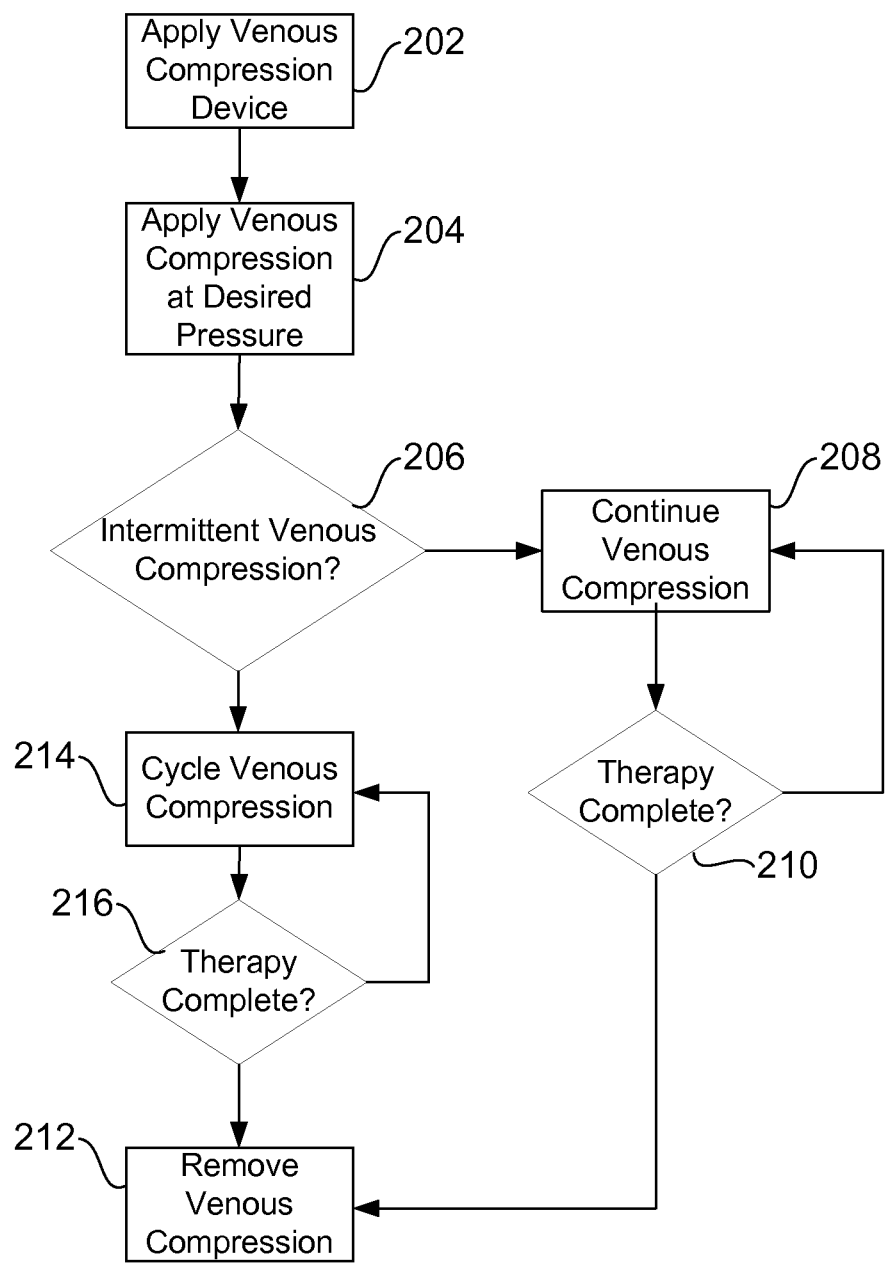
FIG. 9 is a schematic of a process of patient therapy using a patient therapy system described herein.

If the venous compression used with any of the venous compression systems is applied to the limb intermittently or cyclically, the venous compression applied to the limb is increased to the desired pressure and then decreased to a desired pressure according to a regimen selected by the therapist or programmed in a control system. The increase and decrease in the applied pressure is represented at 214 in FIG. 9. The pressure variations can have a repeating cycle, or they can be non-repeating though they may vary from one pressure to another. The therapist or the system evaluates whether the therapy is complete 216, and if not continues the pressure variations as at 214. When the therapy is complete, venous compression is removed 212, and the venous compression cuff removed. The general steps described with respect to FIG. 9 are applicable to any of the venous compression systems described herein.

Figure 7:
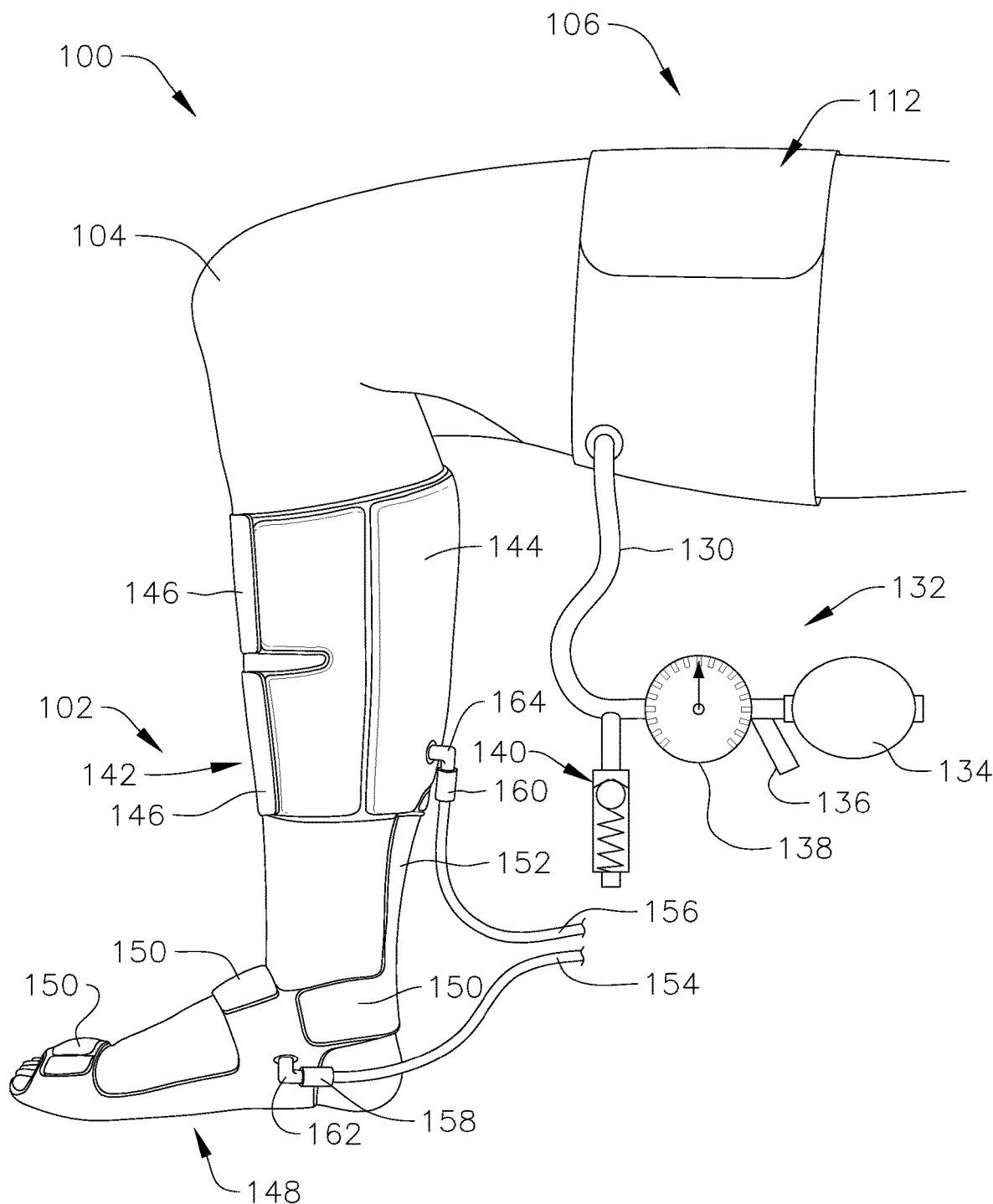
FIG. 7 is a side elevation view of another venous compression apparatus and also showing alternative positions for any venous compression apparatus.

In other examples of venous compression systems, a phlebotomist tourniquet 300 can be applied to the patient's leg 104 (FIG. 7). The locations for applying a tourniquet such as tourniquet 300 include any of those described herein. For example, but not by way of limitation, the tourniquet is applied where a substantial number of veins can be collapsed or where a vein that undergoes reflux can be collapsed through the venous compression applied by the tourniquet. In the example shown in FIG. 1, the tourniquet can be applied proximally of the IPC compression system 102, for example proximally of the proximal-most IPC compression cuff. As illustrated in FIG. 7, the tourniquet can be applied anywhere from below the knee to the groin area, and includes simply by way of example above the ankle, on the calf, at various locations above the knee, as would be understood by one skilled in the art upon reviewing the present description. Additionally, as illustrated in FIG. 13, the tourniquet can be applied at or around an incompetent venous valve, or adjacent or proximal thereto. Other means of selecting the location of a tourniquet can be used. Additionally, multiple tourniquets can be applied to a patient's limb, or combinations of different venous compression devices can be applied to a patient's limb.

The pressure is applied by any of the venous compression systems discussed herein, including a tourniquet 300, can be any of the pressures discussed herein. Additionally, time variations in the applied venous pressure may also be applicable to applied tourniquets, as well as any other venous compression systems discussed herein. The methods or means for determining the location, the pressure magnitude or timing of venous compression application can be according to any of the methods or means considered herein.

In another example of a venous compression system, a venous compression system 400 (FIG. 8) includes a venous cuff 112 such as that described herein. The venous compression system 400 includes a conventional fluid conduit 402, which may be removably coupled to the cuff 112, such as through a suitable coupling or fitting or connector. The other end of the fluid conduit 402 is removably coupled to a respective port on the controller 200. In the present example, generation and control of pressure in the venous compression cuff 112 is achieved through programming, settings or other criteria established in the controller 200 by the therapist or another operator. Through the controller 200, the venous compression system 400 as well as the IPC therapy system 102 or any other accompanying system with the venous compression system 400, if desired, can be controlled automatically, for example in a manner similar to that by which existing IPC systems are controlled. In one example, mechanical switches may be set in the controller 200 to provide the desired location, pressure magnitude and or timing of the venous compression application and other pressure applications. In another example, selections may be made digitally, such as through digital switches (not shown), to provide the desired location, pressure magnitude and/or timing of the venous compression application and other pressure applications. In a further example, the controller 200 may be programmed by computer, processor or other means to provide the desired location, pressure magnitude and/or timing of the venous compression application and other pressure applications. In the example of stored instructions, the instructions can be stored in memory, for example flash memory, read-only memory, or other conventional memory configurations. The controller 200 can be programmed through a conventional interface, including a serial port, USB port, memory slots, or other means for accessing a processor and/or memory inside the controller.

Simply by way of example and not by way of limitation, use of a controller such as controller 200 in combination with the venous compression system 400 allows more reliable control of the venous compression system. The controller also allows more predictable application of pressure at the magnitude and/or timing selected by the user. For example, the use of a controller allows for easier application of intermittent venous compression, easier application of cyclical venous compression, and/or venous compression coordinated with distally applied compression. Additionally, use of a controller makes easier a wider variety of spatial arrangements for pressure application, whether it be application of pressure around the perimeter of the leg, focused pressure application or regional pressure application, or other spatial variations. Similarly, use of the controller makes easier a wider variety of temporal variations in pressure application.

The pressure applied by the venous compression system, such as by any of those described herein, can be static over time, such as from the beginning of therapy to the end of therapy. Static pressure for the venous compression system is represented at 500 in FIG. 10A (P-tourn). However, as noted herein, the pressure applied by the venous compression system can be different over time. The applied pressure can be intermittent with differing time spans and differing pressure magnitudes, cyclical with repeating time spans and/or repeating the pressure magnitudes, or combinations of the foregoing. In another example shown in FIG. 10A, the applied venous compression pressure can vary in magnitude over time. Specifically, the venous compression pressure P-tourn can be any of the venous compression pressure magnitudes described herein, or selected according to any of the criteria described herein. Thereafter, at time t1, the applied venous pressure can drop to a lower magnitude, for example to approximately 0 or to a non-zero magnitude, for example for a selected time period. In one example, the lower pressure magnitude is selected to be a non-zero magnitude at or below a pressure in which no venous compression occurs, which might be termed Pnc. The pressure Pnc can be selected to be a positive pressure allowing the venous compression cuff or other apparatus to remain somewhat inflated or filled, thereby decreasing any subsequent rise time for increasing the pressure to P-tourn or any other selected pressure. In one example, the pressure Pnc can be at or about 20 mm of mercury, or a pressure between about 10 and 20 mm of mercury. At the end of the selected time period, for example at time t2, the applied venous pressure can rise. The resulting applied venous pressure can be the selected compression pressure P-tourn, or the applied venous pressure can be another selected magnitude.

Figure 10A:
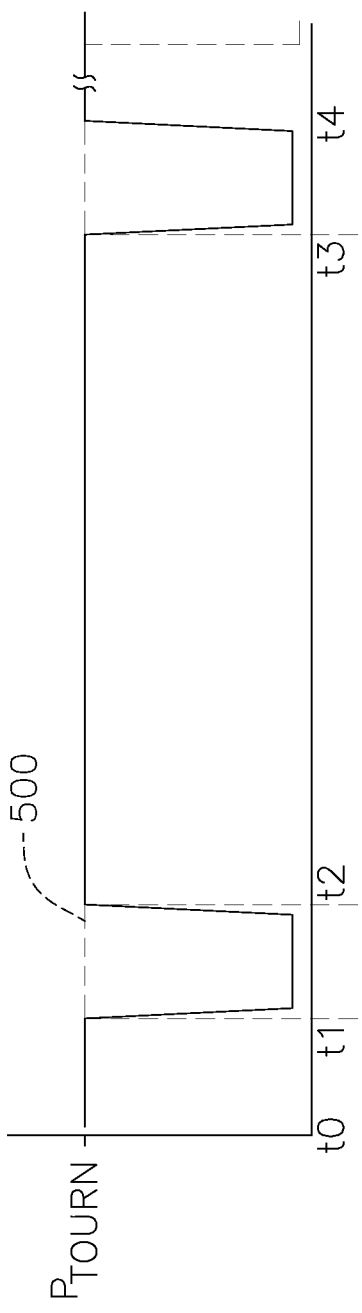
FIGS. 10A and 10B are schematic graphical representations of pressure profiles as a function of time for a venous compression configuration and a vascular assist configuration, respectively.

In the pressure versus time profile represented in FIG. 10A, the selected non-static pressure P-tourn continues for a time period until time t3, at which time in the present example the previously-described pressure changes repeat. The pressure-time profile represented in FIG. 10A results in pressure being applied over time, and the product of the pressure and the time can be expressed as an integral or the area under the pressure versus time profile in FIG. 10A. The integral can be represented as Ptourn-i. The variations in applied venous compression pressure continue as represented in FIG. 9 at 214 and 216 until such time as therapy is complete or discontinued. In other examples, the selected pressures can be different, the time periods represented by t1, t2, and t3 can be different, and the pressure profile can be intermittent or cyclical, as desired. The time period between t1 and t2 can be about three seconds, as depicted in one example in FIG. 10A, but can be as low as approximately 1 second or less, or even zero (static pressure), and as long as approximately 10 or 15 seconds, though the times may depend on the application and the patient. In one example, an upper value for the difference between time t1 and t2 may be a function of the time it takes for venous blood from capillaries to collect in veins. The use of a controller such as controller 200 in FIG. 8 makes easier the selection and application of the venous compression pressure and time combinations. However, it should be understood that pressure and time variations can be accomplished without a controller such as controller 200, for example manually or otherwise.

In another example of a venous compression system, and an example of a therapy system including a therapy system combining a venous compression system with an arterial therapy system, venous compression can be coordinated with arterial compression. Such coordination can be done with any combination of venous compression system and arterial compression systems, including those described herein. In one example, the use of a controller such as controller 200 in FIG. 8 makes easier the coordination of venous compression with arterial compression. The coordination of venous compression with arterial compression is represented schematically in FIGS. 7A and 7B, but it will be understood that these schematic representations can be easily implemented by those skilled in the art in appropriate apparatus and systems upon considering the descriptions herein.

Figure 10B:
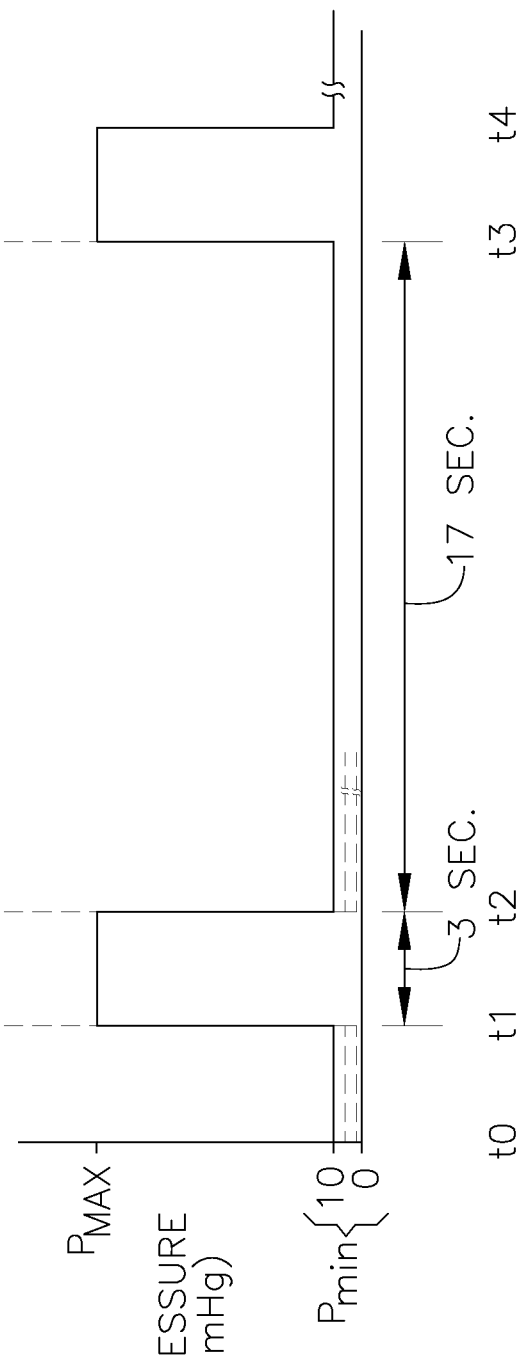

In an example of coordinating venous compression with arterial compression, arterial compression cycles between first and second applied pressures, for example Pmin and Pmax. The times at which arterial compression changes and the time periods therebetween can be illustrated by t1, t2, t3 and t4, which times can be selected as desired. In one example, the lower pressure of the arterial pressure system may be zero or a non-zero number such as 10 mm of mercury. These examples are depicted in FIG. 10B. Additionally, it will be understood by those skilled in the art already familiar with existing arterial compression systems that a lower pressure Pmin may be different for a given bladder within the arterial compression system. For example, the lower applied pressure Pmin for a foot compression bladder may be different than that for a calf compression bladder, either or both of which may be different than that for a thigh arterial compression bladder. Alternatively, the lower applied pressure Pmin may be the same for all arterial compression bladders. The lower applied pressure Pmin can be the lower applied pressure in arterial compression systems or IPC therapy systems conventionally used at the present time. In the case of a single arterial compression bladder, the pressure versus time profile over a given cycle may produce a product of the pressure and time, for example as may be expressed by the integral or the area under the pressure versus time profile in FIG. 10B for a given cycle. That integral may be represented by Pac-i, and for the profiles shown in FIGS. 10A and 10B, it can be seen that Pac-i is less than Ptourn-i. That Pac-i is less than Ptourn-i will apply in a number of venous therapy situations when combined with arterial therapy.

The full applied pressure for an arterial compression system Pmax can also be the maximum applied pressure in arterial compression systems or IPC therapy systems conventionally used at the present time. For example, the applied pressure Pmax can be about 120 mm of mercury, but they are typically over 60 mm of mercury and anywhere between 100 mm of mercury to about 140 mm of mercury or more. The applied pressure Pmax can also be selected as a function of the patient conditions and other indications, as would be known to one skilled in the art.

The times at which the IPC or other arterial therapy system changes pressure are indicated at t1, t2, t3 and t4. In the present example, those times are coincident and can be synchronized with the times represented in FIG. 10A, but they also may be selected to be different in one or more of the times. In the example depicted in FIGS. 7A and 7B, the pressure changes in the venous compression system are coordinated with the pressure changes in the IPC therapy system. In this example, the IPC system is at a low pressure, for example Pmin, and the venous compression system is at a high pressure, for example Ptourn, until time t1. In one example, the venous compression system can remain static at Ptourn, but in the present example the venous compression system applied pressure drops beginning at time t1. The applied IPC pressure increases at the same time, and those pressures remain the same for a selected time period. In the present example, those pressures remain constant for about three seconds, until t2, at which time the venous compression system applies a higher pressure, and the IPC system pressure drops, for example to Pmin. As illustrated in the present example, these pressures remain for approximately 17 seconds until time t3, at which time the pressure changes repeat, and the cycle continues. In another example, the interval between t1 and t2 can be lower, even down to about one second or less, or higher even up to about 10 or 15 seconds. In another example, the interval between t2 and t3 can be less than 17 seconds, even down to about 10 seconds or less, or higher up to tens of seconds and even up to a minute or several minutes. Other times can be selected. Additionally, times for the venous compression system pressure variations can be selected to be different than the times selected for the IPC system pressure variations.

As illustrated in FIG. 10B, the inflation and deflation rates are relatively fast, in accordance with conventional systems. It is desired to have rapid IPC inflation. Also as illustrated in FIGS. 7A and 7B, the start points of the pressure transitions in the venous compression system and the IPC compression system are coincident. In one example, the venous compression system can have its deflation start time delayed relative to the IPC inflation start time (for example t1), and the venous compression system can have its inflation start time advanced relative to the IPC deflation start time (for example t2). Additionally, the rise and decay times of the venous compression system can be configured to be different from those of the IPC system or the same, as desired. The pressure applications for the venous compression system and for the IPC system can then vary, either cyclically or intermittently or otherwise, for example according to the steps 214 and 216 in FIG. 9. Once venous therapy is complete, venous compression is removed at step 212, and the venous compression pressure is removed or zero, as illustrated at the end of FIG. 10A.

An example of a process for applying arterial and venous compression, for example using the apparatus described with respect to FIG. 4, is illustrated in FIG. 11. The example will be described in the context of using the foot, ankle and calf compression devices for arterial compression and using the proximal-most compression device only for venous compression. In the present example, the separate arterial and venous compression devices are applied 602 (FIG. 11) to the patient in the desired configuration. The configuration can be any of those described herein or a configuration that would be apparent to one skilled in the art after considering the present description. For examples other than that described regarding FIG. 4 (not by way of limitation), the arterial compression device can be a foot compression device, an ankle compression device, a calf compression device, thigh compression device, multiples thereof or combinations thereof. However, the present example has the compression devices shown in FIG. 4 are being used.

Once the compression devices are applied and adjusted and configured as desired, therapy is begun. Specifically, arterial and venous compression is applied 604 at the desired pressures, including the pressures and timing described with respect to any of examples discussed herein. As therapy progresses, the system may check 606 if the venous compression is to be intermittent or static. If static, the system cycles the arterial compression and continues 608 the venous compression until therapy is complete 610. If the venous therapy is not complete, the cycling of the arterial compression continues 608. Once complete, venous compression is removed 612, and arterial compression can also be removed, or may be continued if desired.

If venous compression is intermittent, the system cycles 614 the arterial and venous compressions according to the desired or set timing and pressures. Once complete, venous compression is removed 612, and arterial compression can also be removed, or may be continued if desired. Examples of pressure and time profiles used in the process of FIG. 11 are represented in the profiles of FIGS. 10A and 10B.

It is noted at this point that the method described and illustrated in FIG. 11 can apply both to a system and method whereby venous compression is applied with a device separate from that for arterial compression as well as to a system and method whereby venous compression is applied with a device that can also do arterial compression. The structures for doing both can be identical, with the differences arising from the settings for the pressure applied to the compression structure used for venous compression. Conversely, structures for doing both arterial and venous compression can be different (different from those whereby venous compression is applied with a device separate from that for arterial compression), for example in the venous compression device. Where the venous compression device is configured to do both arterial and venous compression, the venous compression device can include discrete bladders, for example, within the same structure (for example within the same cuff). However, in the context of the structure described with respect to FIG. 4, the venous compression device 106 is a single cuff and can be used to achieve both venous and arterial compression by suitable selection of pressures and timing.

Another example of a venous compression system and method, and one for which many of the venous compression devices usable in the applications described herein can also be used, has the venous compression structure also apply arterial compression (the phlebotomist tourniquet being less effective at arterial compression than other examples described herein). In the present example, the apparatus described with respect to the assembly and system of FIG. 4 is used in a way that at least one of the cuffs (and in other examples a plurality of the cuffs) can apply both venous compression and also arterial compression. In the present example, all of the apparatus is the same as that described with respect to FIG. 4 except for the settings or programming for a control system, as would be understood to one skilled in the art. However, it should be understood that other apparatus and combinations of apparatus can be used so that a venous compression device can also apply arterial compression.

A process for applying arterial and venous compression using the same structure for both compressions will be described in the context of FIG. 12. In the apparatus of FIG. 4 when used in a process of FIG. 11 according to settings illustrated in FIG. 12, arterial compression is also applied using apparatus separate from that by which venous compression is applied, but it should be understood that in other examples arterial compression and venous compression can be applied using a single structure rather than separate structures. In such a configuration, the venous compression device can increase blood flow in an arterial mode and occlude venous veins in a venous occlusion mode. In the present example, the arterial mode will be higher pressure and shorter duration than the venous occlusion mode.

Figure 12A:
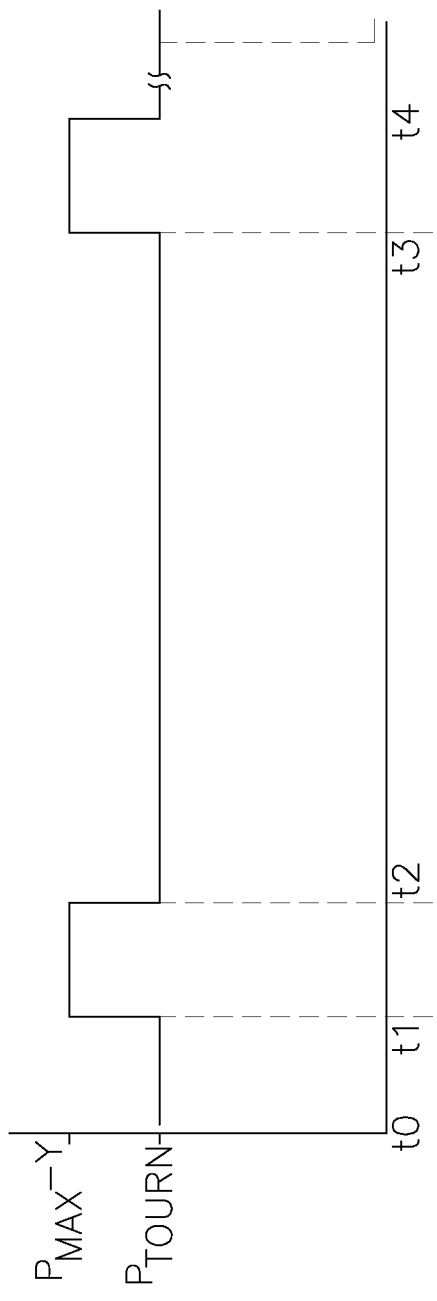
FIGS. 12A and 12B are schematic graphical representations of pressure profiles as a function of time for another venous compression configuration and vascular assist configuration, respectively.
Figure 12B:
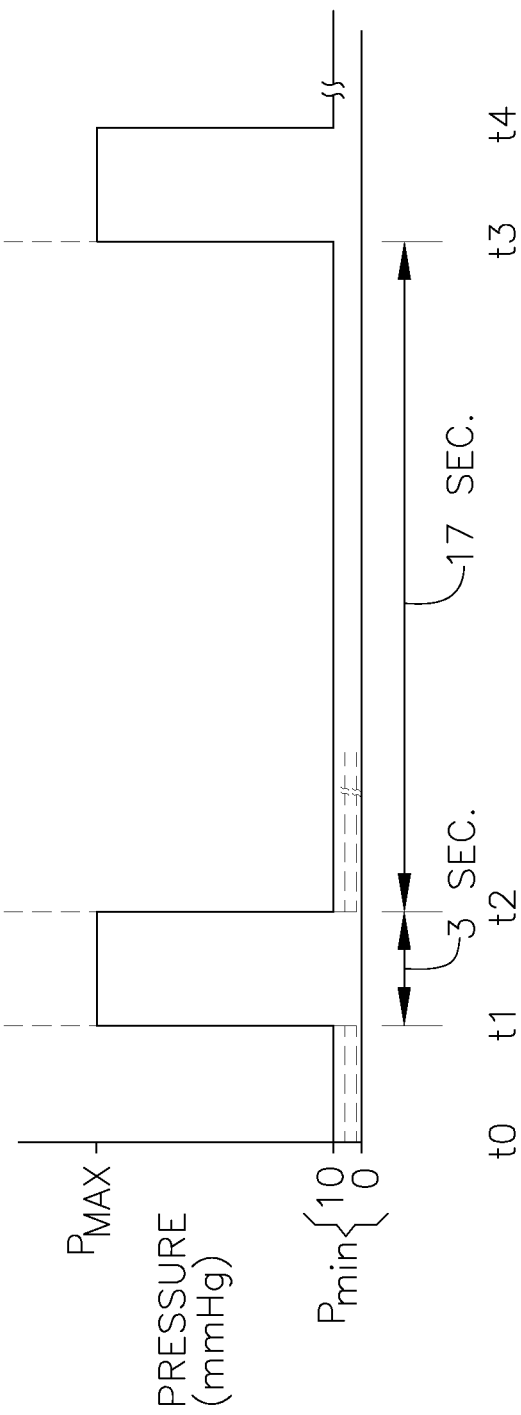

In the example of FIGS. 12A and B, arterial compression cycles between first and second applied pressure is, for example Pmin and Pmax. The times at which arterial compression changes and the time periods there between are indicated by t1, t2, t3 and t4, which times can be selected as desired. The arterial compression arrangement can be the same as or similar to that described with respect to FIG. 10B, or other selected arrangements.

The pressure applied by the venous compression system in the present example is illustrated in FIG. 12A. In the present example, the venous compression pressure is configured to be cyclical and substantially in phase with the arterial compression profile. As with the arrangement described with respect to FIG. 10A, the venous compression pressure P-tourn can be any of the venous compression pressure magnitudes described herein, or selected according to any of the criteria described herein. Thereafter, at time t1, the applied venous pressure rises pressure is represented in FIG. 12A as Pmax-Y. In the present example, Pmax is the full applied pressure for the arterial compression system, represented in FIG. 12B. Also in the present example, the value of Y can be anything from zero to the difference between Pmax and P-tourn, or slightly less than that difference. In the case where the value of Y is zero, the applied pressure for the venous compression device between t1 and t2 is the same as the arterial compression pressure applied through the arterial compression devices. The difference between Pmax and Y may be such as to put the compression pressure at 80 mm of mercury or higher, and for example 100 mm of mercury at least. Alternatively, it can be as high as Pmax. The value of Y can also be greater than the difference, but in such a situation the venous compression device will be at the venous compression pressure or below. In another example, the value of Y can be selected as a function of the distance from the adjacent arterial compression device, or the distance from the foot, or the elevation difference between the heart and the venous compression device.

At the end of the selected time period, at time t2, the applied pressure in the venous compression device falls back to P-tourn. This pressure is maintained until time t3, and the process repeats until therapy is complete or discontinued. In the present example, the time periods for the venous compression device coincide with those for the arterial compression devices. However, it should be understood that the venous compression device time periods can be different. For example, the pressure increase in the venous compression device can be advanced or delayed relative to that for the arterial compression devices. Additionally, the pressure drop in the venous compression device can be advanced or delayed relative to that for the arterial compression devices. The rise times in the venous compression device as well as the decay times can also be different.

In another example of the application of a venous occlusion pressure, a subject 700 (FIG. 13) is shown with a venous occlusion device 702. The venous occlusion device 702 can take any number of forms, including those described herein, and may be controlled by a number of apparatus (not shown in FIG. 13). For example, the venous occlusion device 702 can be an inflation cuff, an elastic band, external stimulation devices, including electrical stimulation systems or other devices. In the example of an inflation cuff, the cuff can be controlled through a conventional inflation bulb, a battery operated pressure controller, or other apparatus. In the present example, the venous occlusion device 702 includes a cuff 704 extending about the subject's leg above the knee. The venous occlusion device 702 alternatively can be placed at other locations on the leg, for example other locations discussed herein. The cuff is secured through conventional means, for example straps, buckles, snaps or other easy to apply fasteners.

In the context of a simple venous occlusion device such as the cuff 704 on the subject 700, venous occlusion can be achieved by inflating the cuff 704 or otherwise reducing the inside diameter of the cuff. The occlusion pressure can be selected as desired, including using one of the criteria described herein, but in one example is sufficient to reduce venous reflux while still allowing a vein to be opened through muscle action, for example through walking as illustrated in FIG. 13. In the present example, the occlusion pressure is applied while the subject is ambulatory. The occlusion pressure is maintained as long as desired, but is relieved at the latest when the subject is no longer ambulating. As discussed herein, other pressures can be used as a venous occlusion pressure, and the applied pressure can be static, intermittent or cyclical.

In the venous occlusion device 702 shown in FIG. 13, the venous occlusion device on the subject 700 includes a detector assembly or a sensor assembly 706. The detector assembly senses when the subject is ambulating. In the present example, the detector assembly includes a motion element 708 coupled at one end 710 to the cuff 704 and at another end 712 to a holding element 714. The holding element 714 may be a band, strap or other element that maintains the lower end 712 relatively stationary on the subject's leg. The upper end 710 is preferably securely held by the cuff 704 in such a way that movement of the motion element 708 during ambulation can be indicated in the assembly. In one example, a motion element 708 may be a linearly inelastic strap that stretches a sensor element, for example attached to the cuff 704. The sensor element (not shown) can sense elongation or flexing of the strap as an indicator of ambulation. Consequently, the sensor element could indicate arterial therapeutic compression produced by the subject walking. With the onset of ATC, venous compression pressure can be applied, for example by inflating the cuff 704, and maintained static or applied intermittently as desired. If the sensor element no longer indicates arterial therapeutic compression, or ATC below a selected threshold, the sensor element can be used to remove venous compression pressure, for example by deflating the cuff.

Other detector or sensor configurations can be used as an ATC detector. In one example, electronic sensors can be used to sense electromyographic activity, for example under the cuff or elsewhere on the leg. Alternatively, muscle size variations can be sensed using for example mercury, indium-gallium alloy or other liquid metal sensors can be used to sense muscle contraction. The sensors can be set to sense a certain magnitude of contraction or a combination of muscle contraction over a selected time period. Other configurations may also be used.

Any of the arterial and/or venous compression systems can be configured to operate according to the time profile examples discussed herein. Additionally, any of the arterial and/or venous compression systems can be configured to operate according to time profiles selected using the considerations discussed herein to fit the desired therapy configuration. Also, use of a controller such as controller 200 makes easier such therapy configurations.

Having thus described several exemplary implementations, it will be apparent that various alterations and modifications can be made without departing from the concepts discussed herein. Such alterations and modifications, though not expressly described above, are nonetheless intended and implied to be within the spirit and scope of the inventions. Accordingly, the foregoing description is intended to be illustrative only.

What is claimed is:

1. A method of applying a vascular therapy to a patient, the method comprising
applying a pressure to a limb of the patient according to a first pressure profile for arterial compression therapy during a first time period that includes a time when the pressure in the first pressure profile changes between a first lower pressure and a first higher pressure, and during a time in the first time period, applying a pressure to the patient's limb according to a second pressure profile wherein the pressure in the second pressure profile changes between a second lower pressure and a second higher pressure during a time before the first pressure profile changes between the first higher pressure and the first lower pressure, and wherein a magnitude of the pressure in the second pressure profile is less than a then-existing arterial pressure and is a collapsing pressure sufficient to substantially collapse a vein in the patient's limb, wherein the applying the pressure according to the first pressure profile includes applying the first pressure profile to the patient's limb distal of the collapsing pressure, wherein the applying the first pressure profile includes applying intermittent pneumatic compression, and wherein the applying the intermittent pneumatic compression includes a first maximum pressure and wherein the collapsing pressure is at least approximately 10 mm of mercury less than the first maximum pressure.

2. A method of applying a vascular therapy to a patient, the method comprising applying a pressure to a limb of the patient according to a first pressure profile for arterial compression therapy and, during at least part of the time of applying the pressure to the limb of the patient according to the first pressure profile for arterial compression therapy, applying a pressure to the patient's limb according to a second pressure profile wherein, when the pressure in the first pressure profile is a maximum, a magnitude of the pressure in the second pressure profile is a collapsing pressure simultaneously less than the first pressure profile maximum and sufficient to substantially collapse a vein in the patient's limb, and wherein as the pressure in the first pressure profile drops below the pressure in the second pressure profile, the pressure in the second pressure profile is sufficient to substantially collapse a vein in the patient's limb.

3. The method of claim 2 further comprising applying the vascular therapy to a patient having venous reflux.

4. The method of claim 3 wherein the applying the pressure according to the first pressure profile includes applying the first pressure profile to the patient's limb distal of the collapsing pressure.

5. The method of claim 4 wherein the applying the pressure according to the first pressure profile includes applying intermittent pneumatic compression.

6. The method of claim 5 wherein the applying the collapsing pressure is applied intermittently and the intermittent pneumatic compression and the collapsing pressure are substantially synchronized.

7. The method of claim 6 wherein the collapsing pressure and the intermittent pneumatic compression have different phases.

8. The method of claim 6 wherein the collapsing pressure and the intermittent pneumatic compression have respective high and low pressures and where the high of the collapsing pressure occurs at a different time than the high of the intermittent pneumatic compression pressure.

9. The method of claim 3 wherein a magnitude of the pressure in the second pressure profile is greater than 20 mm of mercury.

10. The method of claim 9 wherein a magnitude of the pressure in the second pressure profile is between approximately 50 and 70 mm of mercury.

11. The method of claim 3 wherein the applying the pressure to the patient's limb according to the second pressure profile is applied under control of a controller.

12. The method of claim 11 further including applying intermittent pneumatic compression under control of the controller.

13. The method of claim 11 further including generating the collapsing pressure and wherein the generating of the collapsing pressure is programmable.

14. The method of claim 3 further including the patient walking.

15. The method of claim 14 wherein the applying the collapsing pressure is applying the collapsing pressure with a venous tourniquet.

16. The method of claim 14 wherein the patient walking includes the patient walking on a treadmill.

17. The method of claim 2 wherein the applying the pressures according to the first and second pressure profiles includes wherein the first and second pressure profiles are different.

18. The method of claim 17 wherein a pressure in the first pressure profile rises when a pressure in the second pressure profile drops.

19. The method of claim 17 wherein a pressure in the first pressure profile rises when a pressure in the second pressure profile remains substantially constant.

20. The method of claim 2 wherein the applying the pressure to the patient's limb according to the second pressure profile includes applying the pressure using a pressure generating element selected from the group of an electric stimulation device, an inflation cuff, a phlebotomist tourniquet, and an intermittent pneumatic compression device.

21. The method of claim 2 wherein the applying the pressure to the limb of the patient according to the first pressure profile for arterial compression therapy includes applying the pressure using a first pressure generating element having a connection element for connecting to a controller.

22. The method of claim 21 wherein the applying the pressure to the limb of the patient according to the first pressure profile for arterial compression therapy includes applying the pressure using the first pressure generating element wherein the connection element includes a pneumatic connection.

23. The method of claim 21 wherein the applying the pressure to the limb of the patient according to the first pressure profile for arterial compression therapy includes applying the pressure using the first pressure generating element wherein the connection element includes an electrical connection.

24. The method of claim 2 wherein the applying the pressure according to the second pressure profile includes applying a constant pressure during multiple times when the pressure in the first pressure profile drops below the maximum.

25. The method of claim 24 wherein the pressure in the first pressure profile drops below the maximum a plurality of times within one minute.

26. A method of applying a vascular therapy to a patient, the method comprising
   applying a pressure to a limb of the patient according to a first pressure profile for arterial compression therapy having a first maximum pressure for a first duration twice during a first interval and,
   during the time of application of the pressure according to the first pressure profile, applying a second pressure to the patient's limb according to a second pressure profile wherein a second magnitude for a second duration of the second pressure in the second pressure profile is less than the first maximum pressure and is sufficient to substantially collapse a vein in the patient's limb continuously during the first interval, and wherein an integration of the first maximum pressure over the first duration is less than an integration of the second pressure of the second magnitude over the second duration.

27. The method of claim 26 wherein the applying the pressure to the limb of the patient according to the first pressure profile includes applying the pressure to the limb of the patient distal of the application of the pressure to the patient's limb according to the second pressure profile.

28. The method of claim 26 wherein a controller includes a programmable controller and further including using the controller to control applying the second pressure to the patient's limb according to the second pressure profile.

29. The method of claim 28 wherein the controller is configured to control application of the pressure according to the first pressure profile and application of the second pressure according to the second pressure profile, and further including using the controller to control applying the pressure to the patient's limb according to the first pressure profile.

30. The method of claim 26 wherein the first pressure profile integrated over a second time interval is greater than the second pressure profile integrated over the second time interval.

31. The method of claim 26 wherein the applying the pressure to the limb of the patient according to the first pressure profile is a different phase than the applying the second pressure to the limb of the patient according to the second pressure profile.

32. The method of claim 31 wherein the applying the pressure and the second pressure according to different phases includes applying the pressure and the second pressure in opposite phases.

33. The method of claim 26 wherein the applying pressure according to the first pressure profile is synchronized with the applying the second pressure according to the second pressure profile.

34. The method of claim 26 further including applying the second pressure according to the second pressure profile at a magnitude greater than approximately 20 mmHg over an extended period.

35. The method of claim 34 wherein the applying the second pressure over the extended period includes applying the second pressure over an extended period greater than 3 seconds.

36. The method of claim 26 further including applying the second pressure according to the second pressure profile intermittently.

37. The method of claim 36 wherein the applying the second pressure intermittently includes applying pressure through intermittent pneumatic compression.

38. The method of claim 26 wherein the applying the second pressure according to the second pressure profile includes applying a constant pressure during multiple sequential intervals.

39. A method of applying a vascular therapy to a patient, the method comprising applying a pressure to a limb of the patient according to a first pressure profile for arterial compression therapy and applying a pressure to the patient's limb according to a second pressure profile wherein a magnitude of the pressure in the second pressure profile is sufficient to substantially collapse a vein in the patient's limb while reducing the pressure applied for arterial compression, and further including applying pressure according to the first pressure profile such that the first pressure profile has a first maximum pressure and applying pressure according to the second pressure profile such that the second pressure profile has a second maximum pressure, and wherein during at least one time while applying the pressures according to the first and second pressure profiles, the second maximum pressure is simultaneously at least 10 mmHg less than the first maximum pressure.

40. The method of claim 39 wherein the applying the pressure according to the second pressure profile includes applying a constant pressure during multiple sequential instances of reducing the pressure applied for arterial compression.

41. The method of claim 40 wherein the applying the constant pressure occurs over at least a minute.

42. A method of applying a vascular therapy to a patient, the method comprising applying a pressure to a limb of the patient according to a first pressure profile having a first maximum pressure and, while applying the pressure to the limb of the patient according to the first pressure profile, applying a second pressure to the limb of the patient according to a second pressure profile wherein a magnitude of the pressure in the second pressure profile is sufficient to substantially collapse a vein in the patient's limb and is at least approximately 10 mmHg less than the first maximum pressure and at a time when the second pressure in the second pressure profile is sufficient to substantially collapse a vein, the pressure in the first pressure profile decreases.

43. The method of claim 42 further including keeping the second pressure in the second pressure profile substantially constant over multiple times of the pressure in the first pressure profile decreasing.

44. The method of claim 43 wherein the second pressure in the second pressure profile is substantially constant for at least one minute.

45. A method of applying a vascular therapy to a patient, the method comprising applying a pressure to a leg of the patient according to a first pressure profile for arterial compression therapy when the patient is upright and, while applying the pressure to the leg of the patient according to the first pressure profile, applying a pressure to the patient's leg according to a second pressure profile wherein a magnitude of the pressure in the second pressure profile is sufficient to substantially collapse a vein in the patient's leg.

46. The method of claim 45 further including applying a pressure to the leg of the patient when the patient is sitting.

47. The method of claim 45 further including applying a pressure to the leg of the patient when the patient is walking.

48. The method of claim 45 wherein the applying the pressure to the leg of the patient according to the first pressure profile includes applying the pressure to the patient's leg for about three seconds and repeating the application of pressure to the patient's leg after approximately 17 seconds.

49. The method of claim 48 wherein the applying the pressure according to the first pressure profile includes repeating the first pressure profile approximately every 20 seconds including applying the pressure to the patient's leg for about three seconds and not applying the pressure to the patient's leg for about 17 seconds.

50. The method of claim 45 further including keeping the pressure in the second pressure profile substantially constant while increasing and decreasing the pressure to the leg of the patient according to the first pressure profile multiple times.

* * * * *